US007662408B2

United States Patent
Saito et al.

(10) Patent No.: US 7,662,408 B2
(45) Date of Patent: Feb. 16, 2010

(54) SUSTAINED-RELEASE PREPARATIONS

(75) Inventors: Kazuhiro Saito, Osaka (JP); Tomomichi Futo, Osaka (JP); Tetsuo Hoshino, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/530,186

(22) PCT Filed: Feb. 9, 2005

(86) PCT No.: PCT/JP2005/001922

§ 371 (c)(1),
(2), (4) Date: Apr. 4, 2005

(87) PCT Pub. No.: WO2005/074896

PCT Pub. Date: Aug. 18, 2005

(65) Prior Publication Data

US 2006/0074027 A1 Apr. 6, 2006

(30) Foreign Application Priority Data

Feb. 10, 2004 (JP) ............................. 2004-034180

(51) Int. Cl.
*A61K 38/09* (2006.01)
(52) U.S. Cl. ........................................ 424/468; 514/15
(58) Field of Classification Search ........................ None
See application file for complete search history.

(56) References Cited

U.S. PATENT DOCUMENTS

| 4,652,441 | A | 3/1987 | Okada et al. |
| 4,711,782 | A | 12/1987 | Okada et al. |
| 4,728,721 | A | 3/1988 | Yamamoto et al. |
| 4,849,228 | A | 7/1989 | Yamamoto et al. |
| 4,917,893 | A | 4/1990 | Okada et al. |
| 4,954,298 | A | 9/1990 | Yamamoto et al. |
| 5,061,492 | A | 10/1991 | Okada et al. |
| 5,330,767 | A | 7/1994 | Yamamoto et al. |
| 5,476,663 | A | 12/1995 | Okada et al. |
| 5,575,987 | A | 11/1996 | Kamei et al. |
| 5,585,460 | A | 12/1996 | Yamada et al. |
| 5,611,971 | A | 3/1997 | Maedara et al. |
| 5,631,020 | A | 5/1997 | Okada et al. |
| 5,631,021 | A | 5/1997 | Okada et al. |
| 5,643,607 | A | 7/1997 | Okada et al. |
| 5,716,640 | A | 2/1998 | Kamei et al. |
| 5,851,451 | A | 12/1998 | Takechi et al. |
| 5,889,110 | A * | 3/1999 | Hutchinson ................ 525/54.1 |
| 6,036,976 | A | 3/2000 | Takechi et al. |
| 6,045,830 | A | 4/2000 | Igari et al. |
| 6,113,943 | A * | 9/2000 | Okada et al. ................ 424/457 |
| 6,190,700 | B1 | 2/2001 | Okada et al. |
| 6,419,961 | B1 | 7/2002 | Igari et al. |
| 6,506,410 | B1 | 1/2003 | Park et al. |
| 6,699,500 | B2 | 3/2004 | Okada et al. |
| 6,740,634 | B1 | 5/2004 | Saikawa et al. |

FOREIGN PATENT DOCUMENTS

| EP | 1 197 208 A1 | 4/2002 |
| EP | 1 330 293 | 7/2003 |
| EP | 1 399 133 | 3/2004 |
| EP | 1 466 596 A1 | 10/2004 |
| JP | 63-267720 | 11/1988 |
| JP | 4-321622 | 11/1992 |
| JP | 9-500645 | 1/1997 |
| JP | 10-231242 | 9/1998 |
| JP | 2003-206240 | 7/2003 |
| WO | WO 95/03052 A1 | 2/1995 |
| WO | WO 01/74392 A1 | 7/2000 |
| WO | WO 00/40259 | 7/2003 |
| WO | WO 2004/000363 A1 | 12/2003 |

OTHER PUBLICATIONS

Choi, Seung Ho et al., "Hydrophobic ion pair formation between leuprolide and sodium oleate for sustained release from biodegradable polymeric microspheres", *International Journal of Pharmaceutics*, vol. 203, (2000), pp. 193-202.

Korean Drug Insert, "LH-RH Derivative for Monthly Adminstration, Rorelin Depot Injection (leuprorelin acetate 3.75 mg)", (Sold by Hanmi Corporation; prepared on Mar. 13, 2000, revised on Aug. 13, 2002) with its partial English translation.

English translation of Office Action dated Apr. 10, 2009, issued in corresponding Chinese Application No. 200580010382.5, 8 pages.

Conn.Pm. et al., "Gonadotrophin Hormone-Releasing Hormone and the Analogues thereof," Chinese Medicine—Fascicule on Synthetic Drugs, Biochemical Drugs, and Preparations, 1992, 13(2):87-89, with partial English translation.

Yan et al., "Review of the medication of benign prostatauxe," Shanghai Medicine, 1993,12:16-18, with partial English translation.

Zhang et al., "Development in the Hormone Therapy of Endometriosis Patient," Current Advances in Obstetrics and Gynecology, 1998, 7(4):368-371.

Zhou et al., "Clinical Application of Gonadotrophin Hormone-Releasing Hormone Agonist," Chinese Journal of Practical Gynecology and Obstetrics, 1999, 15(12):754-756.

* cited by examiner

*Primary Examiner*—Christopher R. Tate
*Assistant Examiner*—Roy Teller
(74) *Attorney, Agent, or Firm*—Foley & Lardner LLP

(57) ABSTRACT

A sustained release preparation comprising a combination of a microcapsule which gradually releases a GnRH agonist or a salt thereof for a long term, and a microcapsule which gradually releases a GnRH agonist or a salt thereof for a short term.

8 Claims, 3 Drawing Sheets

```
                        SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: DLeu, DAla, DTrp, DSer (tBu), D2Nal or DHis
      (ImBzl)
<220> FEATURE:
<221> NAME/KEY: MOD_RES
<222> LOCATION: (9)..(9)
<223> OTHER INFORMATION: Pro or Pro-NH-C2H5
<220> FEATURE:
<221> NAME/KEY: MOD_RES
<222> LOCATION: (10)..(10)
<223> OTHER INFORMATION: Gly-NH2 or not present
<220> FEATURE:
<223> OTHER INFORMATION: see specification as filed for detailed
      description of substitutions and preferred embodiments

<400> SEQUENCE: 1

Pro His Trp Ser Tyr Xaa Leu Arg Pro Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: DLeu
<220> FEATURE:
<221> NAME/KEY: MOD_RES
<222> LOCATION: (9)..(9)
<223> OTHER INFORMATION: Pro-NH-C2H5

<400> SEQUENCE: 2

Pro His Trp Ser Tyr Leu Leu Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: Ser (tBu)
<220> FEATURE:
<221> NAME/KEY: MOD_RES
<222> LOCATION: (9)..(9)
<223> OTHER INFORMATION: Pro-NH-NH-CO-NH2

<400> SEQUENCE: 3

Pro His Trp Ser Tyr Ser Leu Arg Pro
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: Ser (tBu)
<220> FEATURE:
<221> NAME/KEY: MOD_RES
<222> LOCATION: (9)..(9)
<223> OTHER INFORMATION: Pro-NH-CH2-CH3

<400> SEQUENCE: 4

Pro His Trp Ser Tyr Ser Leu Arg Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (10)..(10)
<223> OTHER INFORMATION: Gly-NH2

<400> SEQUENCE: 5

Pro His Trp Ser Tyr Trp Leu Arg Pro Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
```

<221> NAME/KEY: MOD_RES
<222> LOCATION: (6)..(6)
<223> OTHER INFORMATION: D2Nal
<220> FEATURE:
<221> NAME/KEY: MOD_RES
<222> LOCATION: (10)..(10)
<223> OTHER INFORMATION: Gly-NH2

<400> SEQUENCE: 6

Pro His Trp Ser Tyr Xaa Leu Arg Pro Gly
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: DHis (ImBzl)
<220> FEATURE:
<221> NAME/KEY: MOD_RES
<222> LOCATION: (9)..(9)
<223> OTHER INFORMATION: Pro-NH-CH2-CH3

<400> SEQUENCE: 7

Pro His Trp Ser Tyr His Leu Arg Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (9)..(9)
<223> OTHER INFORMATION: Pro-NH-CH2-CH2-NH2

<400> SEQUENCE: 8

Pro His Trp Ser Tyr Trp Leu Arg Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: 2-Methyl-Trp
<220> FEATURE:
<221> NAME/KEY: MOD_RES

```
<222> LOCATION: (9)..(9)
<223> OTHER INFORMATION: Pro-NH-CH2-CH3

<400> SEQUENCE: 9

Pro His Trp Ser Tyr Trp Leu Arg Pro
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (9)..(9)
<223> OTHER INFORMATION: Pro-NH-CH2-CH3

<400> SEQUENCE: 10

Pro His Trp Ser Tyr Gly Leu Arg Pro
1               5
```

SUSTAINED-RELEASE PREPARATIONS

TECHNICAL FIELD

The present invention relates to a novel sustained-release preparation comprising a combination of a microcapsule which gradually releases a GnRH agonist or a salt thereof for a long term and a microcapsule which gradually releases a GnRH agonist or a salt thereof for a short term.

BACKGROUND ART

Luteinizing hormone-releasing hormone known as GnRH (or LHRH) is released from hypothalamus, and binds to a receptor of pituitary gland. LH (luteinizing hormone) and FSH (follicle-stimulating hormone) which are released thereby, act on gonad to synthesize steroidal hormones.

However, it has been revealed that, when a compound having strong luteinizing hormone-releasing hormone activity is continuously administered, the number of available receptors is decreased and formation of gonad-derived steroidal hormones is inhibited. Utilizing this, a compound having GnRH activity is clinically applied as a remedy for sex hormone dependent diseases such as prostate cancer, prostatomegaly, endometriosis, hysteromyoma, metrofibroma, precocious puberty and breast cancer.

Such compounds as have GnRH activity include, specifically, leuprorelin acetate, buserelin acetate and goserelin acetate, and sustained-release preparations containing them are sold as a remedy for the aforementioned diseases. Preparations containing these compounds have been used initially as a preparation which is administered once per day, thereafter, they have been formulated into sustained-release preparations. Currently, they are sold as a sustained-release preparation for one month, three months or four months. Those sustained-releases preparation are disclosed in EP190833 and EP442671.

As described above, compounds having GnRH activity are widely used as a remedy for prostate cancer. In diseases which slowly progress, in particular, prostate cancer, extension of a releasing term of a preparation is preferable not only from a viewpoint of improvement in therapeutic effect and improvement in QOL (quality of life) of patients, but also from a viewpoint of medical economy due to reduction in care times as an outpatient.

OBJECT OF THE INVENTION

However, it is difficult to produce a preparation exhibiting stable sustained-release over a long term. In particular, when long term sustained-release is stressed on, an amount of drug release at an early stage of administration is deficient and manifestation of effect of an early stage of administration is delayed in some cases. In addition, when an amount of drug release at an early stage of administration is excessive, an amount of drug release at a later stage of a sustained-release term is deficient, and it is difficult to retain stable sustained-release over a long term in some cases.

DISCLOSURE OF INVENTION

In order to attain the aforementioned object, the present inventors intensively studied. Unexpectedly, they found that combining GnRH agonist sustained-release preparations having different sustained-release terms can increase an amount of release at an early stage of administration and provide stable sustained-release over a long term. The present inventors further studied based on these findings, which resulted in completion of the present invention.

That is, the present invention relates to:

[1] A sustained-release preparation comprising a combination of a microcapsule which gradually releases a GnRH agonist or a salt thereof for a long term and a microcapsule which gradually releases a GnRH agonist or a salt thereof for a short term;

[2] The preparation according to [1], wherein the GnRH agonist or a salt thereof is a peptide represented by the formula (SEQ ID NO: 1):

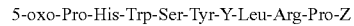

[wherein Y represents a residue selected from DLeu, DAla, DTrp, DSer (tBu), D2Nal and DHis (ImBzl), and Z represents NH—$C_2H_5$ or Gly-$NH_2$]

or a salt thereof;

[3] The preparation according to [1], wherein the GnRH agonist or a salt thereof is an acetate of a peptide represented by the formula (SEQ ID NO: 2):

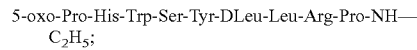

[4] The preparation according to [1], wherein the long term is 5 months or longer, and the short term is shorter than 5 months;

[5] The preparation according to [1], wherein the long term is 5 months or longer and 8 months or shorter, and the short term is 1 week or longer and shorter than 5 months;

[6] The preparations according to [1], wherein the microcapsule is a microcapsule containing a lactic acid polymer or a lactic acid-glycolic acid polymer as a base;

[7] The preparation according to [1], wherein a combination ratio of the microcapsule which gradually releases a GnRH agonist or a salt thereof for a short term and the microcapsule which gradually releases a GnRH agonist or a salt thereof for a long term is 1:about 5 to 1:about 20 expressed as a ratio of a weight of the GnRH agonist or a salt thereof contained in each microcapsule;

[8] The preparation according to [1], wherein:
the microcapsule which gradually releases the GnRH agonist or a salt thereof for a long term is:
a microcapsule containing (i) a GnRH agonist or a salt thereof, and (ii) a lactic acid polymer having a weight average molecular weight of about 18,000 to about 30,000; and
the microcapsule which gradually releases a GnRH agonist or a salt thereof for a short term is:

(1) a microcapsule containing (i) a GnRH agonist or a salt thereof, and (ii) a lactic acid-glycolic acid polymer (75/25 (mol %)) having a weight average molecular weight of 8,000 to about 12,000, or (2) a microcapsule containing (i) a GnRH agonist or a salt thereof, and (ii) a lactic acid polymer having a weight average molecular weight of about 13,000 to about 18,000;

[9] The preparation according to [1], wherein:
the microcapsule which gradually releases a GnRH agonist or a salt thereof for a long term is:
a microcapsule which contains (i) a GnRH agonist or a salt thereof, and (ii) a lactic acid polymer having a weight average molecular weight of about 15000 to about 50000 in which a content of a polymer having a weight average molecular weight of 5000 or less is about 5% or less by weight; and the microcapsule which gradually releases a GnRH agonist or a salt thereof for a short term is:

(1) a microcapsule which contains (i) a GnRH agonist or a salt thereof and (ii) a lactic acid-glycolic acid polymer in which a weight average molecular weight (Mw) is about 8,000 to about 11,500, and a ratio of a weight average molecular weight (Mw) to a number average molecular weight (Mn) is greater than 1.9, and a compositional molar ratio of lactic acid to glycolic acid is 99.9/0.1 to 60/40, and which does not contain a drug retaining substance, or (2) a microcapsule which zero order-releases a GnRH agonist or a salt thereof over 2 months, and which is prepared by microencapsulating a W/O emulsion prepared from an inner aqueous phase solution containing a GnRH agonist or a salt thereof in about 20 to 70% by weight, and an oil phase solution containing, as a release controlling substance, a copolymer or a homopolymer in which a compositional ratio of lactic acid/glycolic acid is 80/20 to 100/0, and a weight average molecular weight is about 7,000 to about 30,000;

[10] The sustained-release preparation according to any one of [1] to [9], which gradually releases a GnRH agonist or a salt thereof for a long term;

[11] The sustained-release preparation according to [10], wherein the long term is 5 months or longer;

[12] An agent for preventing or treating prostate cancer, prostatomegaly, endometriosis, hysteromyoma, metrofibroma, precocious puberty, dysmenorrhea or breast cancer, or a contraceptive agent, which comprises a sustained-release preparation as defined in [1];

[13] A process for producing the sustained-release preparation as defined in [1], which comprises mixing a microcapsule which gradually releases a GnRH agonist or a salt thereof for a long term and a microcapsule which gradually releases a GnRH agonist or a salt thereof for a short term;

[14] A method for preventing or treating prostate cancer, prostatomegaly, endometriosis, hysteromyoma, metrofibroma, precocious puberty, dysmenorrhea or breast cancer, or preventing conception, which comprises administering an effective amount of the sustained-release preparation as defined in [1] to a mammal; and

[15] Use of the sustained-release preparation as defined in [1] for producing a preventive agent or a remedy for prostate cancer, prostatomegaly, endometriosis, hysteromyoma, metrofibroma, precocious puberty, dysmenorrhea or breast cancer, or contraceptive agent.

By combining microcapsules having different sustained-release terms, which gradually release a GnRH agonist or a salt thereof, a preparation having an increased amount of drug release at an early stage of administration and exhibiting stable sustained-release over a long term can be obtained.

BEST MODE FOR CARRYING OUT THE INVENTION

Figure 1:
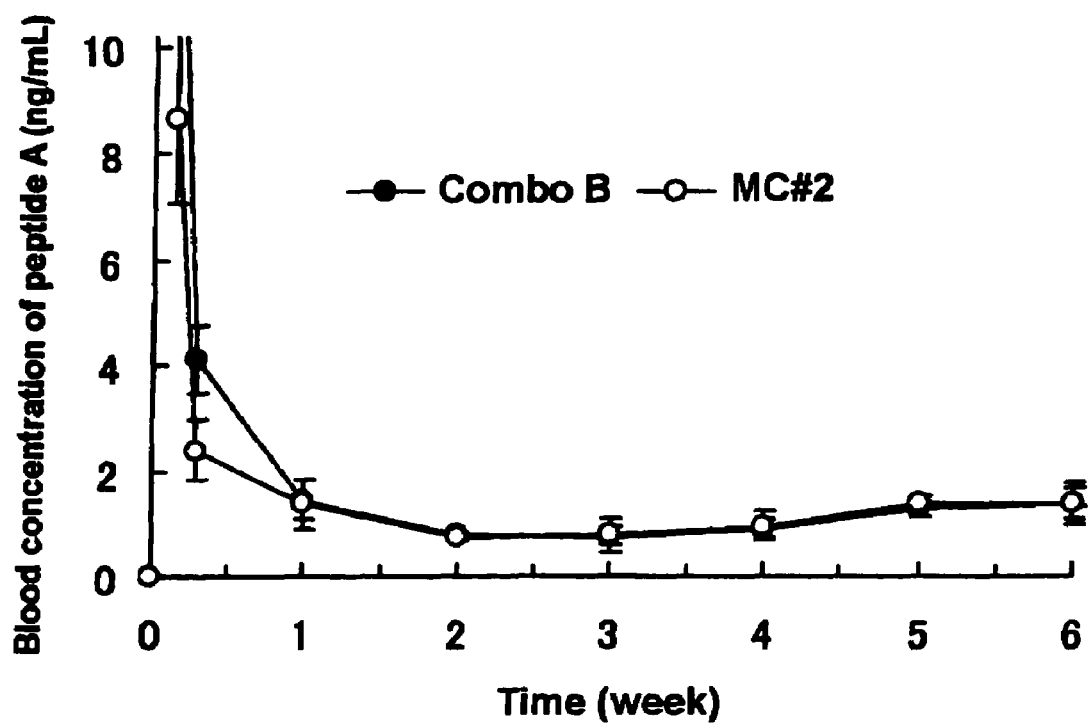
FIG. 1 is a graph showing results of Experimental Example 1. ● denotes a blood concentration of peptide A when combo B is administered, and ○ denotes a blood concentration of peptide A when MC#2 is administered.

The present invention will be described in detail below.

Examples of the GnRH agonist include GnRH agonists which are effective in hormone dependent diseases, in particular, sex hormone dependent cancer (e.g. prostate cancer, uterus cancer, breast cancer, pituitary gland tumor etc.), sex hormone dependent diseases such as prostatomegaly, endometriosis, hysteromyoma, precocious puberty, dysmenorrhea, amenorrhea, premenstrual syndrome, multilocular ovary syndrome, recurrence of said cancer after operation, dwarfism, Alzheimer's disease, menopausal disorder, indefinite complaint, metastasis of said cancer, and calcium•phosphorus metabolic bone disorder, and contraception (or infertility when rebound effect thereof after administration cease is utilized). Further examples include GnRH agonists which are effective benign or malignant tumor being sex hormone independent but GnRH sensitive.

Examples of this GnRH agonist include, for example, peptides and the like described in Treatment with GnRH analogs, Controversies and perspectives [published by The Parthenon Publishing Group Ltd., 1996], JP-A-03-503165, JP-A-03-101695, JP-A-07-97334 and JP-A-08-259460.

As a specific example of the GnRH agonist, a physiologically active peptide represented by the general formula [I] (SEQ ID NO: 1)

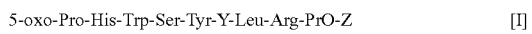

5-oxo-Pro-His-Trp-Ser-Tyr-Y-Leu-Arg-PrO-Z  [I]

[wherein Y represents a residue selected from DLeu, DAla, DTrp, DSer (tBu), D2Nal and DHis (ImBzl) and Z represents NH—$C_2H_5$ or Gly-$NH_2$]

or a salt thereof is used. In particular, a peptide in which Y is DLeu and Z is NH—$C_2H_5$ or a salt thereof (i.e. a peptide represented by 5-oxo-Pro-His-Trp-Ser-Tyr-DLeu-Leu-Arg-Pro-NH—$C_2H_5$ (SEQ ID NO: 2) or a salt thereof, in particular, acetate thereof (leuprorelin acetate: manufactured by Takeda Chemical Industries, Ltd.)) is preferable.

A peptide exemplified as the GnRH agonist may be pharmacologically acceptable salt. When the peptide has a basic group such as an amino group, examples of such salt include salts with inorganic acids (e.g. hydrochloric acid, sulfuric acid, nitric acid, boric acid etc.), and organic acids (e.g. carbonic acid, bicarbonic acid, succinic acid, acetic acid, propionic acid, trifluoroacetic acid etc.).

When the peptides have an acidic group such as a carboxyl group, examples include salts with inorganic bases (e.g. alkali metal such as sodium, potassium etc., alkali earth metal such as calcium, magnesium etc.) and organic bases (e.g. organic amines such as triethylamine etc., basic amino acids such as arginine etc.). The peptides may form a metal complex compound (e.g. copper complex, zinc complex etc.).

These peptides or a salt thereof can be produced by the methods described in the aforementioned publications or gazettes, or methods based on them.

In addition to the aforementioned leuprorelin (leuprorelin acetate), preferable examples of the GnRH agonist include,
(1) Goserelin (SEQ ID NO: 3)
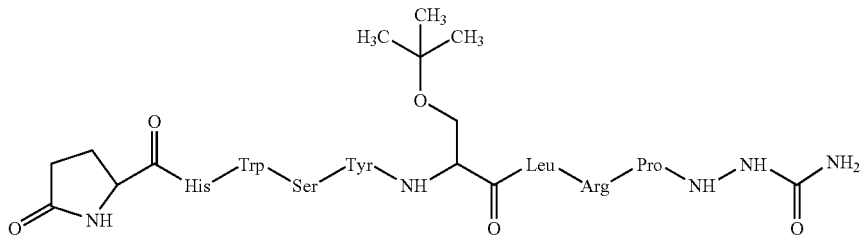
(U.S. Pat. No. 4,100,274, JP-A-52-136172),
(2) Buserelin (SEQ ID NO: 4)
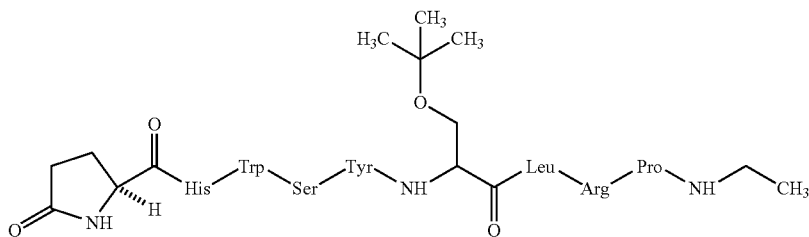
(U.S. Pat. No. 4,024,248, German Patent No. 2438352, JP-A-51-41359),
(3) Triptorelin (SEQ ID NO: 5)
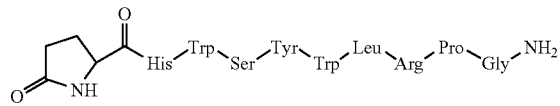
(U.S. Pat. No. 4,010,125, JP-A-52-31073),
(4) Nafarelin (SEQ ID NO: 6)
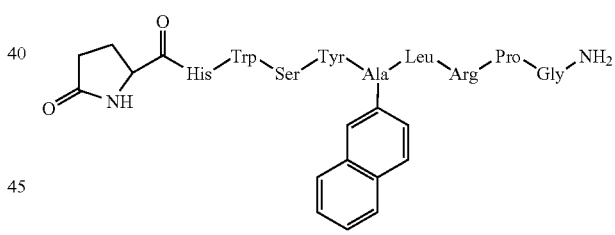
(U.S. Pat. No. 4,234,571, JP-A-55-164663, JP-A-63-264498, JP-A-64-25794),
(5) Histrelin (SEQ ID NO: 7)
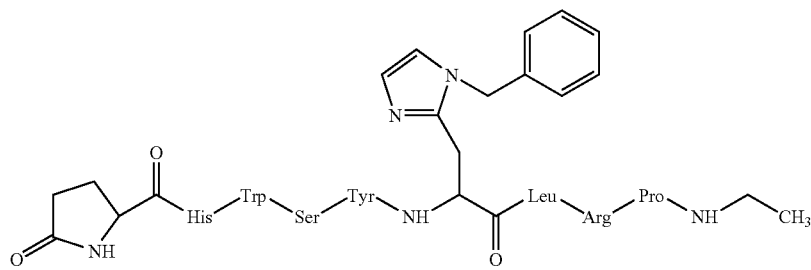

(6) Deslorelin (SEQ ID NO: 8)

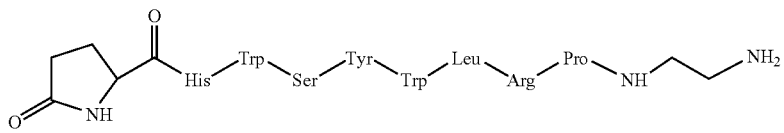

(U.S. Pat. No. 4,569,967, U.S. Pat. No. 4,218,439), (7) Meterelin (SEQ ID NO: 9)

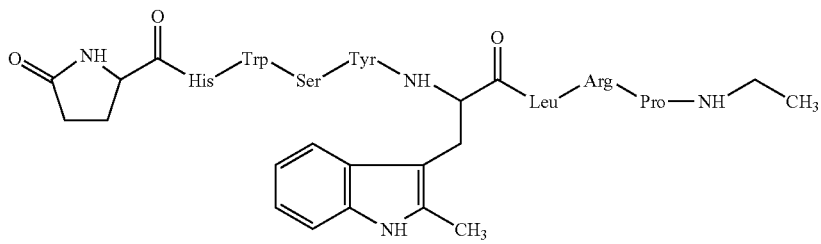

(PCT WO 91/18016), (8) Gonadrelin (SEQ ID NO: 10)

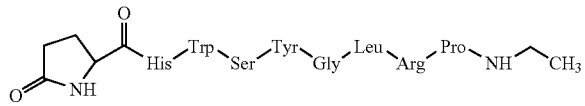

(German Patent No. 2213737)

and salts thereof.

As a microcapsule which gradually releases a GnRH agonist or a salt thereof for a short term (hereinafter, simply referred to as "short term sustained-release microcapsule" in some cases), a microcapsule which gradually releases a GnRH agonist or a salt thereof for a term of shorter than 5 months is used, and a microcapsule which gradually releases a GnRH agonist or a salt thereof preferably for a term of about 1 week or longer and shorter than about 5 months, more preferably for a term of about 2 weeks or longer and about 4 months or shorter, further preferably for a term of about 3 weeks or longer and about 4 months or shorter, further more preferably for a term of about 1 month or longer and about 3 months or shorter, particularly preferably for a term of about 1 month or longer and about 2 months or shorter, or about 2 months or longer and about 4 months or shorter, most preferably for a term of about 1 month to about 3 months is used.

As a microcapsule which gradually releases a GnRH agonist or a salt thereof for a long term (hereinafter, simply referred to as "long term sustained-release microcapsule" in some cases), a microcapsule which gradually releases a GnRH agonist or a salt thereof for a term of 5 months or longer is used, and a microcapsule which gradually releases a GnRH agonist or a salt thereof for a term of preferably 5 months or longer and shorter than 2 years, more preferably for a term of 5 months or longer and one year and 6 months or shorter, further preferably for a term of 5 months or longeand 1 year or shorter, further more preferably for a term of 5 r months or longer and 8 months or shorter, particularly preferably for a term of 5 months or longer and 6 months or shorter, most preferably for a term of about 6 months is used.

In the present invention, as the "microcapsule which gradually releases a GnRH agonist or a salt thereof for a short term" and "microcapsule which gradually releases a GnRH agonist or a salt thereof for a long term", the aforementioned microcapsules having each sustained-release term can be used by appropriately combining them. For example, (i) a microcapsule which gradually releases GnRH agonist or a salt thereof for about 1 month or about 3 months and (ii) a microcapsule which releases GnRH agonist or a salt thereof for about 6 months can be combined to use. Specifically, (i) the sustained-release microcapsule described in EP190833 or EP442671 and (ii) the sustained-release microcapsule described in WO03/002092 can be combined to use.

As used herein, "combined to use" may be successive administration of a preparation containing the short term sustained-release microcapsule (hereinafter, simply referred to as "short term sustained-release preparation" in some cases) and a preparation containing the long term sustained-release microcapsule (hereinafter, simply referred to as "long term sustained-release preparation" in some cases), or simultaneous administration after mixing of the short term sustained-release preparation and the long term sustained-release preparation (in this case, formulation into a preparation after mixing of the short term sustained-release microcapsule and the long term sustained-release microcapsule is included). It also includes administration of the long term sustained-release preparation after a certain term (e.g. after a few hours to a few days) from administration of the short term sustained-release preparation. However, herein, it refers to administration so that sustained-release terms of drugs of a short term sustained-release preparation and a long term sustained-release preparation are overlapped, and administration of another preparation after passage of a sustained-release term of a drug of one preparation is not included in "combined to use" herein. For example, when a one month sustained-release preparation and a three months sustained-release preparation are combined to use, the case where the three months sustained-release preparation is administered after one month passed after administration of the one month sustained-release preparation is not included.

A combination ratio of a short term sustained-release preparation and a long term sustained-release preparation is, expressed as a weight ratio of a GnRH agonist, usually 1 to 40 of the long term sustained-release preparation per short term sustained-release preparation, preferably 5 to 20 of the long term sustained-release preparation per short term sustained-release preparation, more preferably 7 to 18 (particularly, 9 to 16) of the long term sustained-release preparation per short term sustained-release preparation, more preferably 7 to 15 of the long term sustained-release preparation per short term sustained-release preparation, further preferably 9 to 12 of the long term sustained-release preparation per short term sustained-release preparation (when a short term sustained-release microcapsule and a long term sustained-release microcapsule are mixed, and formulated into a preparation, the combinational ratio can be determined by replacing "short term sustained-release preparation" by "short term sustained-release microcapsule", and "long term sustained-release preparation" by "long term sustained-release microcapsule").

The sustained-release preparation of the present invention comprising a combination of a long term sustained-release microcapsule and a short term sustained-release microcapsule can gradually release a GnRH agonist or a salt thereof for a long term.

A long term refers to, for example, 5 months or longer, preferably 5 months or longer and shorter than 2 years, more preferably 5 months or longer and one year and 6 months or shorter, further preferably 5 months or longer and one year or shorter, further more preferably 5 months or longer and 8 months or shorter, particularly preferably 5 months or longer and 6 months or shorter, most preferably about 6 months.

The GnRH agonist, preferably a peptide represented by the formula 5-oxo-Pro-His-Trp-Ser-Tyr-DLeu-Leu-Arg-Pro-NH—$C_2H_5$ (SEQ ID NO: 2) or a salt thereof (hereinafter, simply referred to as "leuprorelin or a salt thereof" in some cases), more preferably leuprorelin acetate is administered as a sustained-release microcapsule, more preferably as an injectable comprising the sustained-release microcapsule.

The preparation can be produced by blending leuprorelin or a salt thereof, more preferably leuprorelin acetate together with the physiologically acceptable known carrier, flavor, excipient, vehicle, antiseptic, stabilizer and binder in the generally acceptable unit dosage form required in practice of pharmacy. As an aqueous solution for injection, for example, an isotonic solution containing physiological saline, glucose and other auxiliary agent (e.g. D-sorbitol, D-mannitol, sodium chloride) is used. An appropriate solubilizeing agent such as alcohol (e.g. ethanol), polyalcohol (e.g. propylene glycol, polyethylene glycol), and a nonionic surfactant (e.g. Polysorbate 80™, HCO-50) may be used jointly. As an oily solution, for example, sesame oil and soybean oil are used, and solubilizing agent such as benzyl benzoate and benzyl alcohol may be used jointly. Said preparation may be mixed with, for example, a buffer (e.g. phosphate buffer, sodium acetate buffer), a soothing agent (e.g. benzalkonium chloride, procaine chloride etc.), a stabilizer (e.g. human serum albumin, polyethylene glycol etc.), a preservative (e.g. benzyl alcohol, phenol etc.), and an antioxidant. The prepared injectable is usually filled into an appropriate sealed container such as an ampul and a vial.

Specifically, a sustained-release preparation (particularly, sustained-release microcapsule) containing the GnRH agonist (preferably leuprorelin or a salt thereof, more preferably leuprorelin acetate) can be produced according to methods known per se, for example, according to the method described in EP190833, EP442671, and WO03/002091 for a short term sustained-release preparation (or short term sustained-release microcapsule), or according to the method described in WO03/002092 for a long term sustained-release preparation (or long term sustained-release microcapsule).

The preparation of the present invention can be produced by mixing a microcapsule which gradually releases a GnRH agonist or a salt thereof for a long term with a microcapsule which gradually releases a GnRH agonist or a salt thereof for a short term. That is, a sustained-release preparation of the present invention comprising a combination of a microcapsule which gradually releases a GnRH agonist or a salt thereof for a long term and a microcapsule which gradually releases a GnRH agonist or a salt thereof for a short term can be produced by separately producing a microcapsule which gradually releases a GnRH agonist or a salt thereof for a long term and a microcapsule which gradually releases GnRH agonist or a salt thereof for a short term, appropriately mixing them at a suitable mixing ratio, and formulating the mixture. Mixing of a long term sustained-release microcapsule and a short term sustained-release microcapsule may be performed before or after a primary drying step and a secondary drying step described later.

However when separately administered at an interval, it is not necessary to mix a microcapsule which gradually releases a GnRH agonist or a salt thereof for a long term and a microcapsule which gradually releases a GnRH agonist or a salt thereof for a short term, and each microcapsule may be formulated into a preparation for administration before using each. Alternatively, two sustained-release preparations comprising short term and long term sustained-release microcapsules, respectively, may be mixed on administration.

One example of a process for producing the sustained-release microcapsule will be described below.

First, a GnRH agonist (preferably leuprorelin or a salt thereof, more preferably leuprorelin acetate) is dissolved in water at about 20 to 70% (W/W), preferably 25 to 65% (W/W), more preferably 35 to 60% (W/W), and if necessary, a drug retaining substance such as gelatin and basic amino acid is dissolved or suspended therein, to obtain an inner aqueous phase solution.

To the inner aqueous phase solution may be added carbonic acid, acetic acid, oxalic acid, citric acid, phosphoric acid, hydrochloric acid, sodium hydroxide, arginine, lysine or a salt thereof as a pH adjusting agent for retaining stability and solubility of a GnRH agonist (preferably leuprorelin or a salt thereof, more preferably leuprorelin acetate). Further, albumin, gelatin, citric acid, sodium ethylenediamine tetraacetate, dextrin, sodium hydrogen sulfite, and polyol compound such as polyethylene glycol as a stabilizer for a GnRH agonist (preferably leuprorelin or a salt thereof, more preferably leuprorelin acetate, or generally used paraoxybenzoic acid esters (methylparaben, propylparaben etc.), or benzyl alcohol, chlorobutanol and thimerosal as a preservative may be added.

The inner aqueous phase solution thus obtained is added to a solution (oil phase) containing a high-molecular polymer (polymer), and emulsification procedure was carried out to make a W/O-type emulsion. As the emulsification procedure, the known dispersing methods, for example, intermittent vibration method, method using a mixer such as a propeller-type stirrer and a turbine-type stirrer, colloid mill method, homogenizer method, and ultrasound irradiation method are used. Then, the thus prepared W/O-type emulsion is subjected to a microencapsulating step, in which in water drying method or phase separation method can be applied. When a microcapsule is produced by the in water drying method, the W/O emulsion is added to a third aqueous phase to form a three-phase emulsion of W/O/W type, then a solvent in an oil phase is evaporated to prepare a microcapsule.

An emulsifier may be added to the aqueous phase of the outer phase. For example, may be generally any emulsifier as far as it forms a stable O/W-type emulsion, and examples include an anionic surfactant (sodium oleate, sodium stearate, sodium laurylsulfate etc.), a nonionic surfactant (polyoxyethylene sorbitan fatty acid ester [Tween 80, Tween 60, Atras Powder], polyoxyethylene castor oil derivative [HCO-60, HCO-50, Nikko Chemicals Co., Ltd.]), and polyvinylpyrrolidone, polyvinyl alcohol, carboxymethylcellulose, lecithin and gelatin one of them may be used alone, or some of them may be used in combination. A concentration of the emulsifier upon use can be appropriately selected from a range of about 0.01% to 20%, more preferably, about 0.05 to 10%.

For evaporating a solvent of an oil phase, a method generally used is adopted. In the method, evaporation is performed by gradually evacuating while stirring with a propeller-type stirrer of a magnetic stirrer, or by regulating a vacuum degree using a rotary evaporator. In this case, at a time that solidification of a high-molecular polymer proceeds to an extent, gradually warming a W/O/W-type emulsion for the purpose of making desorption of a solvent more complete can shorten a necessary time.

The microcapsule thus obtained is taken by centrifugation or filtration, a free GnRH agonist (preferably leuprorelin or a salt thereof, more preferably leuprorelin acetate), a drug retaining substance and an emulsifier which are adhered to a surface of a microcapsule are washed with distilled water several times, dispersed in distilled water again, and lyophilized. Thereupon, an aggregation preventing agent such as sugar may be added. Water and an organic solvent in a microcapsule are desorbed more completely under reduced pressure with warming, if necessary.

In lyophilization, specifically, a sugar is added to the microcapsule thus obtained at about 2 to about 60% by weight relative to the microcapsule, followed by lyophilization. This step is called primary drying step. Then, the material is appropriately heated in a range from a glass transition temperature of a polymer to a temperature about 40° C. higher than the glass transition temperature. This step is called secondary drying step.

Examples of the sugar to be used include D-mannitol, sodium alginate, fructose, dextran, dextrin, sucrose, D-sorbitol, lactose, glucose, maltose, starches, and trehalose. These sugars may be used alone, or may be appropriately used by mixing them. Among them, D-mannitol which is easily lyophilized and has little toxicity is particularly preferable. A method of adding sugar includes, but not limited, dispersing a microcapsule in an aqueous sugar solution well, and simply adding sugar to microcapsule before mixing them with a mixer, etc. An amount of a sugar to be added is preferably about 5 to about 40% by weight relative to a microcapsule. When microcapsule has been already mixed with sugar, for example, sugar is used on or before water drying or spray drying and then mixed, sugar may be added in view of an amount thereof so that total amount is within the aforementioned range.

Lyophilization may be performed according to the known method.

A heating temperature of secondary drying step is preferably in a range from glass transition temperature of a polymer to a temperature about 20° C. higher than the glass transition temperature. Heating temperature is selected so that temperature of a product is usually in a range of about 30 to about 60° C. Herein, a glass transition temperature refers to an intermediate point glass transition temperature obtained when rising at a warming rate of 10 or 20° C. per minutes using a differential scanning calorimeter (DSC).

Heating time of the secondary drying step is not particularly limited, but usually about 1 to about 240 hours, preferably about 10 to about 120 hours, further preferably about 20 to about 72 hours.

Heating temperature, heating time, a degree of drying, and heating method are determined by particle diameter, stability, glass transition temperature, melting point, fusion, and easiness of deformation of microcapsule, stability of a drug contained therein, kind and amount of sugar added thereto, and a degree of dispersity of microcapsule. By thus heating, water and organic solvent in microcapsule can be removed more completely.

When microcapsule is produced by a phase separation method, a coacervating agent is gradually added to the W/O emulsion under stirring to precipitate and solidify a high-molecular polymer.

The coacervating agent may be a polymer-type, mineral oil-type or vegetable oil-type compound which is compatible with a solvent for high-molecular polymer and does not dissolve an encapsulating polymer. Such coacervating agent includes silicone oil, sesame oil, soybean oil, corn oil, cottonseed oil, coconut oil, linseed oil, mineral oil, n-hexane, and n-heptane. These may be used by mixing two or more kinds.

The microcapsule thus obtained is collected by filtration, and washed with heptane repeatedly to remove the coacervating agent. Then, by the same method as that of the in water drying method, a free drug is removed, and a solvent is desorbed. In order to prevent aggregation of particles during washing, an aggregation preventing agent may be added.

The microcapsule obtained above is slightly ground as necessary, and passed through a sieve to remove a too great microcapsule part. A particle diameter of a microcapsule is in a range of about 0.5 to 1000 μm, more preferably it is desired that the particle diameter is in a range of about 2 to 500 μm. When used as an injectable suspension, the particle diameter is in such a range that dispersity and needle penetrating property are satisfied, and it is desirable that the particle diameter is, for example, in a range of about 2 to about 100 μm.

As the high-molecular polymer, a biodegradable polymer, for example, a polymer, a copolymer or a mixture thereof which is synthesized from one or more kinds of α-hydroxycarboxylic acid such as α-hydroxymonocarboxylic acid (e.g. glycolic acid, lactic acid, etc.), α-hydroxydicarboxylic acid (e.g. malic acid), and α-hydroxytricarboxylic acid (e.g. citric acid) and has a free carboxyl group; poly(α-cyanoacrylic acid ester); polyaminoacid (e.g. poly(γ-benzyl-L-glutamic acid), etc.); maleic anhydride-based copolymer (e.g. styrene-maleic acid copolymer, etc.) are used.

Binding manner of monomer may be any of random, block and graft. When the α-hydroxymonocarboxylic acid, α-hydroxydicarboxylic acid, or α-hydroxytricarboxylic acid has an optically active center in a molecule, any of D-, L- and DL-isomers may be used. Among them, a lactic acid-glycolic acid polymer (hereinafter, referred to as poly(lactide-co-glycolide), poly(lactic acid-co-glycolic acid) or a lactic acid-glycolic acid copolymer in some cases and, unless indicated otherwise, homopolymer (polymer) and copolymer of lactic acid and glycolic acid are called collectively. In addition, lactic acid homopolymer is called lactic acid polymer, polylactic acid, or polylactide, and glycol acid homopolymer is called glycolic acid polymer, polyglycolic acid, or polyglycolide in some cases), and poly(α-cyanoacrylic acid ester) are preferable. Further preferable is a lactic acid-glycolic acid polymer, and more preferable is a lactic acid-glycolic acid polymer having a free carboxyl group at an end.

A biodegradable polymer may be a salt. Examples of the salt include salts with inorganic bases (e.g. alkali metal such as sodium and potassium, alkaline earth metal such as calcium and magnesium) and organic bases (e.g. organic amines such as triethylamine, basic amino acids such as arginine), and salts and complex salts with transition metals (e.g. zinc, iron, copper, etc.).

When lactic acid-glycolic acid polymer is used as a biodegradable polymer, its compositional ratio (mole %) is preferably about 100/0 to about 40/60, more preferably about 100/0 to about 50/50. In the case of sustained-release microcapsule which zero order-releases a GnRH agonist over 2 months, a lactic acid homopolymer (lactic acid polymer) having a compositional ratio of 100/0 is also preferably used.

An optical isomer ratio of lactic acid which is one of minimum repetition units of the "lactic acid-glycolic acid polymer" is preferably such that D-isomer/L-isomer (mole/mole %) is in a range of about 75/25 to about 25/75. For this D-isomer/L-isomer (mole/mole %), in particular, the polymer having a range of about 60/40 to about 30/70 is generally used.

A weight average molecular weight of the "lactic acid-glycolic acid polymer" or "lactic acid polymer" is usually about 3,000 to about 100,000, preferably about 3,000 to about 60,000, further preferably about 3,000 to about 50,000.

In the present invention, for example, a preparation using a lactic acid-glycolic acid polymer (75/25 (mole %)) with a weight average molecular weight of 8,000 to 12,000 or a lactic acid polymer having a weight average molecular weight of 13,000 to 18,000 as a base of a short term sustained-release microcapsule, and a preparation using a lactic acid polymer with a weight average molecular weight of 18,000 to 30,000 as a base of a long term sustained-release microcapsule can be combined.

Dispersivity (weight average molecular weight/number average molecular weight) is usually, preferably about 1.2 to about 4.0, particularly preferably about 1.5 to about 3.5.

An amount of a free carboxyl group of the "lactic acid-glycolic acid polymer" or "lactic acid polymer" is usually preferably about 20 to about 1000 μmol (micromoles), particularly preferably about 40 to about 1000 μmol (micromoles) per unit mass (gram) of the polymer.

The weight average molecular weight, number average molecular weight and dispersivity above are molecular weight in terms of polystyrene measured by gel permeation chromatography (GPC) using polystyrenes having the known molecular weights as standard substance, and calculated dispersivity. The standard substance includes, for example, the following combinations:

(1) polystyrenes having the known weight average molecular weights of around 500, around 1,000, around 3,000, around 5,000, around 10,000, around 20,000, around 50,000 and around 100,000 (hereinafter, standard substance A)

(2) 10 kinds of polystyrenes having the known weight average molecular weights of around 500, around 1,000, around 2,500, around 5,000, around 10,000, around 20,000, around 50,000 around 100,000, around 200,000 and around 400,000 (hereinafter, standard substance B)

(3) 8 kinds of polystyrenes having the known weight average molecular weights of 98900, 37200, 17100, 9490, 5870, 2500, 1051 and 495 (hereinafter, standard substance C).

Measurement is performed by using a GPC apparatus (HLC-8120GPC manufactured by Tosoh Corporation; a detector is a differential refractometer), and a GPC column (manufactured by Tosoh Corporation, a column in which TSK gel G4000H$_{HR}$, TSK gel G3000H$_{HR}$, TSK gel G2000H$_{HR}$ and TSK gel G1000H$_{HR}$ are connected from a sample inlet in an order from a great exclusion limit), and using tetrahydrofuran as a mobile phase. A flow rate is 1.0 mL/min.

The amount of the free carboxyl group above refers to that obtained by labeling method (hereinafter, referred to as "amount of carboxyl group by labeling method"). Specifically, the case of polylactic acid is as follows. W mg of polylactic acid is dissolved in 2 mL of a mixed solution of 5N hydrochloric acid/acetonitrile (v/v=4/96), 2 mL of 0.01 M o-nitrophenylhydrazine hydrochloride (ONPH) solution (5N hydrochloric acid/acetonitrile/ethanol=1.02/35/15), 2 mL of 0.15 M 1-ethyl-3-(3-dimethylaminopropyl)-carbodimide hydrochloride solution (pyridine/ethanol=4v/96v) are added and reacted at 40° C. for 30 minutes, and the solvent is distilled off. The residue is washed with water (4×), dissolved in 2 mL of acetonitrile, and 1 mL of 0.5 mol/L ethanolic potassium hydroxide solution is added and reacted at 60° C. for 30 minutes. The reaction solution is diluted with 1.5N aqueous sodium hydroxide solution to Y mL, and 544 nm absorbance A (/cm) is measured using a 1.5N aqueous sodium hydroxide solution as a control. On the other hand, when using a DL-lactic acid aqueous solution as a standard substance, an amount of its free carboxyl group Cmol/L is obtained by alkali titration, and 544 nm absorbance of DL-lactic acid hydrazide in ONPH labeling method is B (/cm), a molar quantity of free carboxyl group per unit mass (gram) of a polymer can be obtained by the following equation:

$$[COOH](mol/g) = (AYC)/(WB)$$

Alternatively, although the "amount of carboxyl group" may also be obtained by dissolving the biodegradable polymer in a toluene-acetone-methanol mixed solvent, and titrating the carboxyl group in this solution with an alcoholic potassium hydroxide solution using phenolphthalein as an indicator (hereinafter, a value obtained by this method is referred to as "amount of carboxyl group by alkali titration method"). However, the reaction competes with hydrolysis of the polyester main chain during titration, as a result, there is a possibility that the titration end point becomes unclear, and therefore it is desirable to determine by the labeling method.

The "lactic acid-glycolic acid polymer" or "lactic acid polymer" can be produced, for example, by dehydration polycondensation without catalyst from lactic acid and glycolic acid, or from lactic acid (JP-A-61-28251) or ring opening polymerization using a catalyst from a cyclic diester compound such as lactide and glycolide, or lactide (Encyclopedic Handbook of Biomaterials and Bioengineering Part A: Materials, Volume 2, Marcel Dekker, Inc., 1995). The polymer obtained by the aforementioned known ring opening polymerization method does not necessarily have a free carboxyl group at an end of the resulting polymer, but by subjecting to a hydrolyzing reaction described in EP-A-0839525, it can be modified into a polymer having an extent of an amount of a carboxyl group per unit mass, and this can be also used.

The "lactic acid-glycolic acid polymer having a free carboxyl group at an end" or "lactic acid polymer having a free carboxyl group at an end" above can be produced by the same process as the known process (for example, see dehydration polycondensation method without catalyst, JP-A-61-28521, JP-A-10-182496, JP-A-2000-234016) or a similar process.

More specifically, as a long term sustained-release microcapsule, a microcapsule (A) described, for example, in WO 03/002092, containing (i) a GnRH agonist or a salt thereof and (ii) a lactic acid polymer having a weight average molecular weight of about 15000 to about 50000 in which a content of a polymer having a weight average molecular weight of not more than 5000 is not more than about 5% by weight is used.

In the microcapsule (A), a content of a GnRH agonist or a salt thereof is, for example, about 0.001 to about 50% (w/w), preferably about 0.02 to about 40% (w/w), further preferably about 0.1 to about 30% (w/w), more preferably about 0.1 to about 24% (w/w), particularly preferably about 3 to about 24% (w/w), most preferably about 14 to about 24% (w/w) relative to a whole preparation.

A lactic acid polymer is preferably a polymer in which a content of a polymer having a molecular weight of not more than 5000 is not more than about 5% by weight and a content of a polymer having a molecular weight of not more than 3000 is not more than about 1.5% by weight, further preferably a polymer in which a content of a polymer having a molecular weight of not more than 5000 is not more than 5% by weight, a content of a polymer having a molecular weight of not more than 3000 is not more than about 1.5% by weight, and a content of a polymer having a molecular weight of not more than 1000 is not more than about 0.1% by weight.

A weight average molecular weight of a lactic acid polymer is preferably 15000 to 40000, further preferably about 15000 to about 30000, more preferably about 17000 to about 30000.

The weight average molecular weight in this case can be determined, for example, using said standard substance B.

A short term sustained-release microcapsule to be used is, for example, (1) a microcapsule (B) containing (i) a GnRH agonist or a salt thereof and (ii) a lactic acid-glycolic acid polymer wherein a weight average molecular weight (Mw) is about 8,000 to about 11,500, a ratio of the weight average molecular weight (Mw) to the number average molecular weight (Mn) is greater than 1.9, and a compositional molar ratio of lactic acid to glycolic acid is 99.9/0.1 to 60/40, and not containing a drug retaining substance, or (2) a microcapsule described in EP442671 (C) which zero order-releases a GnRH agonist or a salt thereof over 2 months, which is prepared by microencapsulating a W/O emulsion prepared from an inner aqueous phase solution containing about 20 to 70% by weight of a GnRH agonist or a salt thereof, and an oil phase solution containing a copolymer or a homopolymer as a release controlling substance, wherein a compositional ratio of lactic acid/glycolic acid is 80/20 to 100/0 and the weight average molecular weight is about 7,000 to about 30,000.

The microcapsule (B) is a novel microcapsule, preferably, it is a microcapsule produced by mixing (i) a solution containing a GnRH agonist or a salt thereof and not containing a drug retaining substance and (ii) a solution regulated at about 25 to about 35° C., containing a lactic acid-glycolic acid polymer or a salt thereof in which a weight average molecular weight (Mw) is about 8,000 to about 11,500, a ratio of the weight average molecular weight (Mw) and the number average molecular weight (Mn) is greater than 1.9, and a compositional molar ratio of lactic acid to glycolic acid is 99.9/0.1 to 60/40 to produce a W/O-type emulsion at about 25 to about 35° C., cooling this emulsion to about 15 to about 20° C., dispersing the W/O-type emulsion into an aqueous phase to produce a W/O/W-type emulsion, and subjecting the W/O/W-type emulsion to in water drying.

The lactic acid-glycolic acid polymer or a salt thereof used in the microcapsule (B) is a lactic acid-glycolic acid polymer or a salt thereof in which the weight average molecular weight (Mw) is about 8,000 to about 11,500, a ratio of the weight average molecular weight (Mw) of the lactic acid-glycolic acid polymer to the number average molecular weight (Mn) of the lactic acid-glycolic acid polymer is greater than 1.9, and a relative molar ratio of lactic acid to glycolic acid is 99.9/0.1 to 60/40.

Examples of the salt of the lactic acid-glycolic acid polymer include salts with inorganic bases (e.g. alkali metal such as sodium and potassium, alkaline earth metal such as calcium and magnesium) and organic bases (e.g. organic amines such as triethylamine, basic amino acids such as arginine), and salts and complex salts with transition metals (e.g. zinc, iron, copper etc.).

A ratio (Mw/Mn) of a weight average molecular weight (Mw) of the lactic acid-glycolic acid polymer to a number average molecular weight (Mn) of the lactic acid-glycolic acid polymer is preferably about 1.95 to about 4.0, about 2.0 to about 3.5, further preferably about 2.3 to about 3.1.

A compositional ratio (mole %) of the lactic acid-glycolic acid polymer is preferably 99/1 to 60/40, more preferably 90/10 to 60/40, further preferably 80/20 to 60/40, particularly preferably 80/20 to 70/30 and, inter alia, 75/25 is preferable.

The weight average molecular weight of the lactic acid-glycolic acid polymer is usually about 8,000 to about 11,500, preferably about 9,000 to about 11,500, further preferably about 9,500 to about 11,000.

As used herein, a weight average molecular weight, a number average molecular weight and dispersivity refer to a molecular weight (weight average and number average) in terms of polystyrene measured by gel permeation chromatography (GPC) using a few kinds of polystyrenes having particular weight average molecular weights as standard substance, and calculated dispersivity. A column and a mobile phase used in the measurement can be appropriately selected. A lactic acid-glycolic acid copolymer is dissolved in dichloromethane, added water, and partitioned. A number average molecular weight can be calculated by titrating a dichloromethane layer with an ethanolic potassium hydroxide solution using an automatic titrating apparatus, and calculating an amount of terminal carboxylic acid. Hereinafter, this is expressed as a number average molecular weight by terminal group quantitation. A number average molecular weight by terminal group quantitation is an absolute value, while a number average molecular weight by GPC measurement is a relative value varying depending on assay or analysis conditions (e.g. a kind of a mobile phase, a kind of a column, a standard substance, selection of a slice width, selection of a baseline, etc.), therefore, it is difficult to digitalize it primarily. However, for example, in a polymer synthesized from lactic acid and glycolic acid by dehydration polycondensation method without catalyst and having a free carboxyl group at the end, a number average molecular weight by GPC measurement and a number average molecular weight by terminal group quantitation are approximately consistent. In the case of this lactic acid-glycolic acid polymer, approximately consistent refers to that a number average molecular weight by terminal group quantitation is in a range of about 0.2 to about 1.5-fold of a number average molecular weight by GPC measurement, preferably in a range of about 0.3 to about 1.2-fold.

A GPC method of Reference Example 5 is a GPC method measuring using 8 kinds of polystyrene standard products (standard substance C) having a weight average molecular weight (Mw) of 98900, 37200, 17100, 9490, 5870, 2500, 1051 and 495 assessed by a GPC method.

The weight average molecular and the number average molecular weight of said lactic acid-glycolic acid polymer or a salt thereof used in the microcapsule (B) can be measured, for example, using a GPC method of Reference Example 5.

More specifically, the following lactic acid-glycolic acid polymers are preferably used:

(1) lactic acid-glycolic acid copolymer (lactic acid/glycolic acid=75/25, Mw=about 10300, Mn=about 4000, Mw/Mn ratio=2.6 (a value by a GPC method (old method) of Reference Example 5))

(2) lactic acid-glycolic acid copolymer (lactic acid/glycolic acid=75/25, Mw=about 10400, Mn=about 4100, Mw/Mn ratio=2.5 (a value by a GPC method (old method) of Reference Example 5))

Although a degradation and/or elimination rate of lactic acid-glycolic acid polymer varies greatly depending on composition or molecular weight of the polymer. Generally, as a glycolic acid fraction is lower, degradation and/or elimination is slower, therefore, a release term can be extended by reducing the glycolic acid fraction or increasing the molecular weight. Conversely, the release term can be shortened by increasing the glycolic acid fraction, or reducing the molecular weight. In order to obtain a long term (e.g. 1 to 12 months, preferably 1 to 6 months)-type sustained-release preparation, a lactic acid-glycolic acid polymer having a compositional ratio and a weight average molecular weight in the aforementioned range is preferable. When a lactic acid-glycolic acid polymer which is degraded more rapidly than the lactic acid-glycolic acid polymer having the compositional ratio and the weight average molecular weight in the aforementioned range is selected, control of release at an early stage is difficult. Conversely, when the lactic acid-glycolic acid polymer which is degraded more slowly than the lactic acid-glycolic acid polymer having the compositional ratio and the weight average molecular weight in the aforementioned range is selected, a term during which an effective amount of a drug is not released is easily generated.

A lactic acid-glycolic acid polymer can be produced, for example, by non-catalytic dehydration polycondensation from lactic acid and glycolic acid (JP-A-61-28521) or ring opening polymerization using a catalyst from a cyclic form such as lactide and glycolide (Encyclopedic Handbook of Biomaterials and Bioengineering Part A: Materials, Volume 2, Marcel Dekker, Inc., 1995).

Although a polymer synthesized by ring opening polymerization is a polymer having no carboxyl group, a polymer in which an end is converted into a free carboxyl group by chemically treating the polymer (J. Controlled-Release, vol. 41, p. 249-257, 1996) may also be used.

The lactic acid-glycolic acid polymer having a free carboxyl group at its end can be produced by the known process (for example, dehydration polycondensation method without catalyst, see JP-A-61-28521) with no problem and, further, a polymer having a free carboxyl group at the site not limited to its end can be produced by the known process (for example, see WO94/15587).

As the lactic acid-glycolic acid polymer of which the end has been converted into a free carboxyl group by chemical treatment after ring opening polymerization, those commercially available, for example, from Boehringer Ingelheim KG may be used.

Further, hydrolysis of the lactic acid-glycolic acid polymer produced by ring opening polymerization is performed in the presence of an acid or a base according to the known method. In addition, hydrolysis is performed in the presence of water.

Herein, the acid includes inorganic acids such as hydrochloric acid, nitric acid, sulfuric acid and phosphoric acid, and organic acids such as lactic acid, acetic acid, tartaric acid, citric acid and succinic acid. The base includes alkali metal hydroxide such as sodium hydroxide and potassium hydroxide, and alkali metal carbonate such as sodium carbonate and potassium carbonate. When hydrolysis is performed in the presence of a base, release of a GnRH agonist or a salt thereof from the sustained-release microcapsule is affected by a remaining amount of the base. Therefore, it is preferable to perform hydrolysis in the presence of an acid.

Hydrolysis is usually performed in a solvent which has no adverse effect on the reaction. Such solvent includes alcohols such as methanol, ethanol and propanol, ethers such as tetrahydrofuran, dioxane, diethyl ether and diisopropyl ether, water, and a mixed solvent thereof. Alternatively, an excessive amount of the acid or base above may be used as a solvent.

A temperature upon hydrolysis is, for example, about 0 to about 100° C., preferably about 10 to about 100° C.

Since time necessary for hydrolysis is different depending on weight average molecular weight of polylactic acid produced by ring opening polymerization, kind of an acid or base, kind of solvent, and temperature, the time may be appropriately determined by collecting a part of lactic acid-glycolic acid polymer during hydrolysis, and measuring weight average molecular weight of the collected lactic acid-glycolic acid polymer. Time necessary for hydrolysis is not particularly limited, but is for example about 1 hour to about 10 days, preferably about 10 hours to about 5 days.

The lactic acid-glycolic acid polymer produced by ring opening polymerization can produce only a sustained-release microcapsule having great initial burst, but in a hydrolyzed lactic acid-glycolic acid polymer, that is, the lactic acid-glycolic acid polymer used in the present invention, a sustained-release microcapsule having small initial burst can be produced.

It is preferable that the hydrolyzed lactic acid-glycolic acid polymer is further subjected to a purification step. A purification step is performed by dissolving the hydrolyzed lactic acid-glycolic acid polymer, pouring the resulting solution into water or a mixed solution of water and a water-soluble organic solvent, and separating precipitated lactic acid-glycolic acid polymer.

The organic solvent includes, for example, halogenated hydrocarbons (e.g. dichloromethane, chloroform, chloroethane, dichloroethane, trichloroethane, carbon tetrachloride etc.), ketones (e.g. acetone etc.), ethers (e.g. tetrahydrofuran, ethyl ether, isopropyl ether etc.), esters (e.g. ethyl acetate, butyl acetate etc.), and aromatic hydrocarbons (e.g. benzene, toluene, xylene etc.). An amount of the organic solvent used is, for example, about 3 to about 20-fold (w/v) relative to hydrolyzed polylactic acid.

The water-soluble organic solvent includes, for example, acetone, methanol, ethanol, tetrahydrofuran and acetonitrile. An amount of water or a mixed solution of water and a water-soluble organic solvent to be used is not particularly limited, but is usually a greatly excessive amount relative to hydrolyzed polylactic acid.

A temperature in a purification step is usually about 0 to bout 90° C., preferably about 20 to about 70° C.

By the purification step described above, water-soluble low-molecular compounds (e.g. compounds having a weight average molecular weight of about 1,000 or smaller) can be removed. When a lactic acid-glycolic acid polymer obtained via such purification step is used, an uptake rate (trap rate) of a GnRH agonist or a salt thereof upon production of a sustained-release microcapsule can be enhanced, and a sustained-release preparation having reduced initial burst can be produced.

Further, bringing the lactic acid-glycolic acid polymer produced by ring opening polymerization to hydrolysis and the purification step allows to produce the lactic acid-glycolic acid polymer substantially free of a harmful catalyst (e.g. zinc compound such as zinc oxide and tin compound such as stannous octanoate) used upon ring opening polymerization.

A drug retaining substance is a substance having a characteristic that it is water-soluble but hardly soluble in an organic solvent in an oil phase, becomes a semi-solid which is already highly viscous in the state where dissolved in water, or the viscosity is remarkably increased by some extrinsic factor such as a temperature, a pH, a metal ion (e.g. $Cu^{2+}$, $Al^{3+}$, $Zn^{2+}$ etc.), an organic acid (e.g. tartaric acid, citric acid, tannic acid etc.) or a salt thereof, and a chemical condensing agent (e.g. glutaraldehyde, acetoaldehyde etc.) to become a semi-solid or solid matrix.

As an example of the drug retaining substance, natural or synthetic gums or high-molecular compounds are used.

The natural gum includes acacia gum, gum arabic, Irish moss, karaya gum, tragacanth gum, guaiac gum, xanthan gum, and locust bean gum. The natural high-molecular compound includes a protein such as casein, gelatin, collagen, albumin (e.g. human serum albumin), globulin, and fibrin, and a carbohydrate such as cellulose, dextrin, pectin, starch, agar, and mannan. These may be as they are, or may be a partially chemically modified synthetic gum, for example, the aforementioned natural gum which has been esterified or etherized (e.g. methylcellulose, ethylcellulose, carboxymethylcellulose, gelatin succinate, etc.), or hydrolyzed (e.g. sodium alginate, sodium pectinate etc.), or a salt thereof.

The synthetic high-molecular compound includes, for example, polyvinyl compound (e.g. polyvinylpyrrolidone, polyvinyl alcohol, polyvinyl methyl ether, polyvinyl ether, etc.), polycarboxylic acid (e.g. polyacrylic acid, polymethacrylic acid, Carbopol (Goodrich), etc.), a polyethylene compound (e.g. polyethylene glycol, etc.), a polysaccharide (e.g. polysucrose, polyglucose, polylactose, etc.) and a salt thereof.

In addition, such a substance that can proceed in condensation or crosslinking by the aforementioned extrinsic factor to result in a high-molecular compound is also included.

Among these compounds, inter alia, gelatin, albumin, pectin or agar, in particular, gelatin corresponds thereto.

The microcapsule (B) may contain micro particle (that is, microsphere) containing GnRH agonist or a salt thereof and lactic acid-glycolic acid polymer or a salt thereof. Examples of the microparticle include a microcapsule containing one core of a GnRH agonist or a salt thereof in one particle, a polynuclear microcapsule containing many cores of a GnRH agonist or a salt thereof in one particle, and a microparticle in which a molecular-like GnRH agonist or a salt thereof is dissolved or dispersed in a raw lactic acid-glycolic acid polymer as a solid solution.

A content of a GnRH agonist or a salt thereof in the microcapsule (B) is different depending on kind of GnRH agonist or a salt thereof, desired pharmacological effect and duration of effect, and is for example about 0.1 to about 50% (w/w), preferably about 0.1 to about 30% (w/w), preferably about 5 to about 24% (w/w).

A process for producing the microcapsule (B) will be described in detail below.

The microcapsule (B) is produced by mixing (i) a solution containing a GnRH agonist or a salt thereof, and not containing a drug retaining substance and (ii) a solution, regulated at about 25 to about 35° C., containing a lactic acid-glycolic acid polymer or a salt thereof (hereinafter, abbreviated as biodegradable polymer) in which a weight average molecular weight (Mw) is about 8,000 to about 11,500, a ratio of a weight average molecular weight (Mw) to a number average molecular weight (Mn) is greater than 1.9, and a compositional molar ratio of lactic acid to glycolic acid is 99.9/0.1 to 60/40, to produce a W/O-type emulsion at about 25 to about 35° C. (primary emulsification), cooling this to about 15 to about 20° C., dispersing the W/O-type emulsion in an aqueous phase to produce a W/O/W-type emulsion (secondary emulsification), and subjecting the W/O/W-type emulsion to in water drying.

A W/O-type emulsion containing a solution containing a GnRH agonist or a salt thereof, and not containing a drug retaining substance as an inner aqueous phase, and a solution, regulated at about 25 to about 35° C., containing a biodegradable polymer as an oil phase can be produced as follows.

First, a GnRH agonist or a salt thereof is dissolved in water (preferably distilled water for injection) to a concentration of about 0.001 to about 90% (w/w), preferably about 0.01 to about 80% (w/w), further preferably about 1 to about 70% (w/w), particularly preferably about 50%, to form an inner aqueous phase.

To the inner aqueous phase may be added carbonic acid, acetic acid, oxalic acid, citric acid, phosphoric acid, hydrochloric acid, sodium hydroxide, arginine, lysine and a salt thereof as a pH adjusting agent for keeping stability and solubility of a GnRH agonist or a salt thereof. Further, albumin, gelatin, trehalose, citric acid, sodium ethylenediamine tetraacetate, dextrin, cyclodextrin ($\alpha$-, $\beta$-, $\gamma$-) and a derivative thereof (e.g. maltosyl $\beta$-cyclodextrin, $\beta$-cyclodextrin sulfobutyl ether, etc.), sodium hydrogen sulfite, a polyol compound such as polyethylene glycol, polyoxyethylene sorbitan fatty acid ester [e.g. Tween 80, Tween 60 (Kao Corporation, Japan)], a surfactant such as polyoxyethylene castor oil derivative [e.g. HCO-60, HCO-70 (Nikko Chemicals Co., Ltd.)], paraoxybenzoic acid esters (e.g. methylparaben, propylparaben etc.), benzyl alcohol, chlorobutanol, and thimerosal may be added as a stabilizer for a GnRH agonist or a salt thereof.

The thus obtained inner aqueous phase, and the solution (oil phase) containing the biodegradable polymer regulated at about 25 to about 35° C. are mixed, and the resulting mixture is subjected to the emulsification step to prepare the W/O-type emulsion.

As the solution (oil phase) containing biodegradable polymer, a solution in which a biodegradable polymer is dissolved in an organic solvent is used. The organic solvent may be a solvent which has a boiling point of about 120° C. or lower, is hydrophobic, and dissolves the biodegradable polymer. The solvent includes halogenated hydrocarbons (e.g. dichloromethane (methylene chloride), chloroform, chloroethane, dichloroethane, trichloroethane, carbon tetrachloride, etc.), fatty acid esters (e.g. ethyl acetate, butyl acetate, etc.), ethers (e.g. ethyl ether, isopropyl ether, etc.), and aromatic hydrocarbons (e.g. benzene, toluene, xylene, etc.). Alternatively, two or more kinds of these organic solvents may be used by mixing at an appropriate ratio. The organic solvent is preferably methylene chloride.

A concentration of a biodegradable polymer in the organic solvent is different depending on kind and molecular weight of the biodegradable polymer, and kind of an organic solvent, and is usually about 0.01 to about 90% (w/w), preferably about 0.1 to about 80% (w/w), further preferably about 1 to about 70% (w/w), particularly preferably about 35%.

In order to change compatibility with an inner aqueous phase, and distribution of an organic solvent into an outer aqueous phase, and volatilization of an organic solvent, a partially hydrophilic organic solvent such as ethanol, acetonitrile, acetone and tetrahydrofuran may be added to an oil phase. In addition, in order to dissolve or stabilize a GnRH agonist or a salt thereof in the interior, a surfactant such as sugar fatty acid ester may be added.

The oil phase thus obtained is usually used after removing bacteria and dusts by filtering with a filter. In addition, depending on stability of a biodegradable polymer, a solution containing a biodegradable polymer may be stored in a sealed container at room temperature or in cold places.

A ratio of mixing a solution containing a GnRH agonist or a salt thereof and not containing a drug retaining substance, and a solution of a biodegradable polymer is such that the latter is about 0.1 to about 1000 parts by weight, preferably about 1 to about 100 parts by weight, further preferably about 1 to about 20 parts by weight, particularly preferably about 10 parts by weight per 1 part by weight of the former.

Being different depending on kind of a GnRH agonist or a salt thereof, desired pharmacological effect and duration of effect, mixing may be performed so that a ratio of a GnRH agonist or a salt thereof relative to a biodegradable polymer is about 0.01 to about 50% (w/w), preferably about 0.5 to about 40% (w/w), more preferably about 0.1 to about 30% (w/w), particularly preferably about 10%.

An emulsification step is performed by the known dispersing method, for example, an intermittent vibration method, a method using a stirrer such as a propeller-type stirrer and a turbine-type stirrer, a colloid mill method, a homogenizer method, and an ultrasound irradiation method.

A solution containing a GnRH agonist or a salt thereof and not containing a drug retaining substance and a solution containing the biodegradable polymer are mixed under a temperature of about 25 to about 35° C., preferably about 27 to about 33° C. By this temperature adjustment, a sustained-release microcapsule having better spherical property and/or needle penetrating property can be produced.

A preferable aspect of the emulsification step will be described. For example, first, a solution containing a biodegradable polymer is added to a container containing a solution containing a GnRH agonist or a salt thereof and not containing a drug retaining substance, and the container is vibrated or swung, thereby rough emulsification is performed. In rough emulsification, it is preferable that a temperature of a mixture of the solution containing a GnRH agonist or a salt thereof and not containing a drug retaining substance, and a temperature of the solution containing the biodegradable polymer is adjusted to about 25 to about 35° C., preferably about 27 to 33° C.

Since an object of the rough emulsification is generally to facilitate an emulsification step (precise emulsification) of next step, and a stirring time and vibration and swinging number are not particularly defined. Therefore, when precise emulsification is performed uniformly, the rough emulsification step may be omitted.

Then, the mixture after rough emulsification is subjected to the emulsification step (precise emulsification) with a propeller-type stirrer. In precise emulsification, it is preferable that a temperature of a mixture of a solution containing a GnRH agonist or a salt thereof and not containing a drug retaining substance, and a temperature of a solution containing a biodegradable polymer is adjusted at about 25 to about 35° C., preferably about 27 to about 33° C. By this temperature adjustment, a sustained-release microcapsule having better spherical property and/or needle penetrating property can be produced. An emulsification time at precise emulsification can be selected depending on properties of a GnRH agonist or a salt thereof, and a biodegradable polymer, generally, emulsification is performed in a range of about 0.1 to about 60 minutes.

A volume of an oil phase to be mixed relative to a volume of an inner aqueous phase is about 1 to about 1000-fold, preferably about 2 to about 100-fold, more preferably about 3 to about 10-fold.

A viscosity range of the resulting W/O emulsion is generally about 10 to about 10,000 cp, preferably about 100 to about 5,000 cp, particularly preferably about 500 to about 2,000 cp at about 12 to about 25° C.

It is preferable that the W/O-type emulsion obtained by precise emulsification is cooled in a water bath or the like at about 0 to about 18° C., and a temperature of the W/O-type emulsion is adjusted at about 0 to about 30° C., preferably about 10 to about 25° C., further preferably about 15 to about 20° C.

Then, the W/O-type emulsion thus obtained is dispersed in an aqueous phase (hereinafter, abbreviated as outer aqueous phase) to produce a W/O/W-type emulsion, and the W/O/W-type emulsion is subjected to in water drying to produce a sustained-release microcapsule.

An emulsifier may be added to the outer aqueous phase. As the emulsifier, any emulsifier may be used as far as it generally form a stable O/W emulsion, and examples include an anionic surfactant (e.g. sodium oleate, sodium stearate, sodium laurylsulfate, etc.), a nonionic surfactant (e.g. Tween 80, Tween 60, HCO-60, HCO-70, etc.), polyvinyl alcohol, polyvinylpyrrolidone, and gelatin. These emulsifiers may be used by mixing two or more kinds at an appropriate ratio. In the case of the process of the present invention, preferably, polyvinyl alcohol is used as an emulsifier.

A concentration of an emulsifier in an outer aqueous phase is, for example, about 0.001 to about 20%, preferably about 0.01 to about 10%, further preferably about 0.05 to about 5%, particularly preferably about 0.1%.

An osmotic pressure adjusting agent may be added to the outer aqueous phase. As the osmotic pressure adjusting agent, any agent exhibiting an osmotic pressure when put into an aqueous solution may be used.

Examples of the osmotic pressure adjusting agent include polyhydric alcohols, monohydric alcohols, monosaccharide, disaccharide, oligosaccharide, amino acids or a derivative thereof, and sodium chloride.

As the polyhydric alcohols, for example, trihydric alcohols such as glycerin, pentahydric alcohols such as arabitol, xylitol, adonitol, and hexahydric alcohols such as mannitol, sorbitol, and dulcitol are used. Inter alia, hexahydric alcohols are preferable and, in particular, mannitol is suitable.

Examples of the monohydric alcohols include methanol, ethanol and isopropyl alcohol and, among them, ethanol is preferable.

As the monosaccharides, for example, pentose such as arabinose, xylose, ribose and 2-deoxyribose, and hexose such as glucose, fructose, galactose, mannose, sorbose, rhamnose, fucose are used and, among them, tetrose is preferable.

As the oligosaccharide, for example, trisaccharides such as maltotriose and raffinose saccharides, and tetrasaccharides such as stachyose are used and, among them, trisaccharides are preferable.

As the derivative of monosaccharides, disaccharides and oligosaccharides, for example, glucosamine, galactosamine, glucuronic acid, and galacturonic acid are used.

As the amino acids, any amino acids can be used as far as they are L-isomer, and examples include glycine, leucine and arginine. Among them, L-arginine is preferable.

These osmotic pressure regulators may be used alone, or may be used by mixing them.

These osmotic pressure regulators are used at such a concentration that an osmotic pressure of the outer aqueous phase becomes about 1/50 to about 5-fold, preferably about 1/25 to about 3-fold, further preferably about 1/12 to about 2-fold an osmotic pressure of a physiological saline.

Specifically, in the case where the osmotic pressure regulator is a nonionic substance, a concentration of the osmotic pressure regulator in the outer aqueous phase is about 0.01 to about 60% (w/w), preferably about 0.01 to about 40% (w/w), more preferably about 0.05 to about 30% (w/w), particularly preferably about 0.5 to about 1.5% (w/w). In the case where the osmotic pressure regulator is an ionic substance, a concentration obtained by dividing the aforementioned concentration by a whole ionic valency is used. A concentration of the osmotic pressure regulator to be added is not necessary to be not higher than solubility, and a part of the regulator may be in the dispersed state.

By adding the osmotic pressure regulator to the outer aqueous phase, dispersity of the produced microcapsule can be improved. Its extent is not particularly limited, but for example, it is preferable that about 400 to 700 mg of the microcapsule can be dispersed in 1.5 mL of a dispersing medium for injection in less than 2 minutes.

Removal of an organic solvent may be performed according to the known method. Examples of such the method include a method of removing the solvent under a normal temperature or gradually reduced pressure while stirred with a propeller-type stirrer or a magnetic stirrer, and a method of removing the solvent using a rotary evaporator while a vacuum degree and a temperature are regulated.

The sustained-release microcapsule thus obtained is collected by centrifugation, filtration or a wet cyclone, etc., washed with distilled water repeatedly several times to remove a free GnRH agonist or a salt thereof, a drug retaining substance and an emulsifier which is adhered to a surface of a microcapsule. Then, the washed microcapsule is dried under reduced pressure, or is redispersed in distilled water before lyophilized to remove an organic solvent.

During a preparation step, in order to prevent aggregation of particles, an aggregation preventing agent may be added. As the aggregation preventing agent, for example, water-soluble polysaccharides such as mannitol, lactose, glucose, and starches (e.g. corn starch), amino acids such as glycine, and proteins such as fibrin and collagen are used. Among them, mannitol is preferable.

An amount of the aggregation preventing agent such as mannitol to be added is usually 0 to about 24% by weight relative to a whole microcapsule.

It is preferable that the sustained-release microcapsule of the present invention contains an excipient. It is desired that the excipient is low in toxicity even when administered to a living body, is easily dried such as by lyophilization and, is rapidly dissolved when administered to a living body, or is dissolved upon use. Such excipient includes, for example, sugar, cellulose derivative, amino acid, protein, polyacrylic acid derivative, organic salt, and inorganic salt. These excipients may be used by mixing two or more kinds at an appropriate ratio.

Herein, examples of the sugar include D-mannitol, sodium alginate, fructose, dextran, dextrin, white sugar, D-sorbitol, lactose, glucose, maltose, starches, and trehalose.

Examples of the cellulose derivative include carboxymethylcellulose, hydroxypropylmethylcellulose, ethylcellulose, hydroxymethylcellulose, hydroxypropylcellulose, cellulose acetate phthalate, hydroxypropylmethylcellulose phthalate, and hydroxymethylcellulose acetate succinate.

Examples of the amino acid include glycine, alanine, tyrosine, arginine, and lysine.

Examples of the protein include fibrin, collagen and albumin.

Examples of the polyacrylic acid derivative include sodium polyacrylate, and methacrylic acid/acrylic acid copolymer (Eudragit; manufactured by Rohm Pharma, German).

Examples of the organic salt include sodium citrate, sodium tartrate, sodium carbonate, and potassium carbonate.

Examples of the inorganic salt include sodium chloride, potassium chloride, sodium phosphate, and potassium phosphate.

As the excipient, water-soluble polymers in which a polymer as a base for a sustained-release microcapsule is not dissolved, for example, polyvinylpyrrolidone, and polyvinyl alcohol in addition to the aforementioned excipients are used.

The excipient is preferably sugars and, inter alia, D-mannitol which is easily lyophilized and has little toxicity is preferable.

An amount of the excipient used is determined by solubility of the excipient, and tonicity, viscosity, dispersity and stability of a solution obtained by dissolving the excipient. The excipient is used so that, when a sustained-release microcapsule is dried, a content of the excipient in a dried sustained-release microcapsule is for example about 0.5 to about 99% (w/w), preferably about 1 to about 90% (w/w), more preferably about 2 to about 60% (w/w). When D-mannitol is used as the excipient, it is preferable that a content of the excipient in a dried sustained-release microcapsule is about 0.2 to about 40% (w/w), preferably about 15% (w/w).

By adding these excipients, the following excellent effects are obtained: 1) a frequency of contact and collision of particles during and after drying of a sustained-release microcapsule is reduced, and thereby uniformity of particles at lyophilization is retained, 2) it becomes possible to dry a sustained-release microcapsule at a temperature of a glass transition point or higher, and thereby to remove water or an organic solvent more completely, 3) stability of a sustained-release microcapsule with time is improved, and thereby a sustained-release microcapsule which is better in dispersity, and is not limited to storage in cold places, for example, has a long term use limit at room temperature is obtained.

The microcapsule (B) containing an excipient can be produced, for example, by mixing a microcapsule obtained by the aforementioned in water drying method, and an excipient. The microcapsule may be a microcapsule which has been dried under reduced pressure after washing, or may be a microcapsule which has been redispersed in distilled water after washing, and lyophilized. A method of mixing is not particularly limited, for example, mixing is performed using a mixer.

Further, the microcapsule (B) containing an excipient can be also produced by using an aqueous excipient solution in an outer aqueous phase upon production of a W/O/W-type emulsion used in an in water drying method.

The microcapsule (B) containing an excipient is preferably produced by washing a microcapsule obtained by an in water drying method, dispersing the washed microcapsule in distilled water in which an excipient has been dissolved or suspended, and subjecting the dispersion to lyophilization or drying under reduced pressure. Alternatively, the washed microcapsule may be dispersed in distilled water, and an excipient may be dissolved or suspended in the resulting dispersion, followed by lyophilization or drying under reduced pressure. Inter alia, a uniform mixture is obtained by dispersing the washed microcapsule in distilled water in which an excipient has been dissolved, or dissolving an excipient in a dispersion obtained by dispersing the washed microcapsule in distilled water, and subjecting this to lyophilization.

Further, water and an organic solvent in a microcapsule can be removed more completely and, at the same time, sustained-release can be improved by heating a microcapsule obtained by the aforementioned in water drying method, if desired, to a temperature of a glass transition temperature (Tg) of a polymer used as a base or higher and to such a temperature that each particle in the microcapsule is not adhered mutually. In this case, it is preferable that an organic solvent is removed to less than about 1000 ppm, preferably less than about 500 ppm, more preferably less than about 100 ppm.

A glass transition temperature refers to an intermediate point glass transition temperature obtained when rising at a warming rate of 10 or 20° C. per minutes using a differential scanning calorimeter (DSC).

A timing of heating is preferably after optional addition of an excipient, and after lyophilization or drying under reduced pressure of a microcapsule, being not limiting. For example, heating may be performed after subdivision.

When a heating temperature is lower than a glass transition temperature of a polymer used as a base, removal of water or an organic solvent is insufficient in some cases. On the other hand, when a heating temperature is too high, since risk of fusion and deformation of a microcapsule, and degradation and deterioration of a GnRH agonist or a salt thereof is increased. Thus, a heating temperature can not be unconditionally defined, but can be appropriately determined in view of physical properties of a polymer used as a base (e.g. molecular weight, stability etc.), an average particle diameter and a heating time of a GnRH agonist or a salt thereof, and a microcapsule, and a drying extent, and a heating method of a microcapsule.

A heating temperature is preferably in a range from a glass transition temperature of a polymer used as a base to a temperature about 40° C. higher than the glass transition temperature, preferably from the glass transition temperature of the polymer to a temperature about 35° C. higher than the glass transition temperature, further preferably from the glass transition temperature of the polymer to a temperature about 25° C. higher than the glass transition temperature, particularly preferably from the glass transition temperature of the polymer to a temperature about 20° C. higher than the glass transition temperature.

A heating time is different depending on a heating temperature and an amount of a microcapsule to be treated and, generally, is about 6 to about 120 hours, further preferably about 12 to about 96 hours after a temperature of a microcapsule itself has reached a predetermined temperature. In addition, an upper limit of a heating time is not particularly limited as far as an amount of a remaining organic solvent and moisture become an acceptable value or lower. However, under condition of a glass transition temperature or higher, the microcapsule is softened and deformed by physical contact of microcapsules or loading at lamination of microcapsules. Therefore it is preferable that heating is rapidly terminated when a remaining of an organic solvent and moisture becomes an acceptable value or lower.

A heating method is not particularly limited, but any method may be used as far as it can heat a microcapsule uniformly. Preferable examples of the heating method include a method of performing heating and drying with a lyophilizing machine or a reduced pressure constant temperature machine under reduced pressure.

A particle diameter of the microcapsule (B) is sufficient as far as it is in such a range that its dispersity and needle penetrating property are satisfied, and is for example 0.1 to about 1000 μm, preferably about 1 to about 300 μm, further preferably about 5 to about 150 μm as expressed by an average diameter.

The microcapsule (B) is excellent in desolvation property because a desolvation rate in production is high, for example, a remaining methylene chloride concentration in a preparation after completion of an in water drying step (e.g. after 3 hours) is usually about 2,000 ppm to about 20,000 ppm.

Further, the microcapsule (B) has an excellent characteristic of a slow sedimentation rate. The sedimentation rate can be determined, for example, by filling 50 mg of microcapsule (B) powder in a vial, suspending in 5 ml of a dispersing medium, dispersing about 40 μl of the resulting suspension in 5 ml of a dispersing medium, and measuring NTU with a turbidity meter. The microcapsule (B) has a characteristic that, letting turbidity immediately after suspension to be 100%, a time until a turbidity of 50% is long.

In the microcapsule (C), a compositional ratio of lactic acid/glycolic acid is preferably 90/10 to 100/0, particularly preferably 100/0.

A weight average molecular weight of a copolymer or a homopolymer is preferably about 7,000 to about 25,000 when a compositional ratio of lactic acid/glycolic acid is 100/0, about 7,000 to about 30,000 when the ratio is 90/10, and about 12,000 to about 30,000 when the ratio is 80/20.

A weight average molecular weight in this case can be determined using, for example, standard substance A described above.

A concentration of a GnRH agonist or a salt thereof in an inner aqueous phase solution is usually about 20 to 70% (w/w), preferably about 25 to 65% (w/w), more preferably 35 to 60% (w/w).

A concentration of a copolymer or a homopolymer in an oil phase solution is usually about 0.5 to 90% (w/w), preferably about 2 to 60% (w/w).

A term during which a GnRH agonist or a salt thereof is zero order-released is preferably 2 months or longer and 4 months or shorter, more preferably about 3 months.

As the long term sustained-release microcapsule (A), specifically, a microcapsule (MC) #2 produced in Reference Example 2 described later is used.

As the short term sustained-release microcapsule (B), specifically, a microcapsule (MC) #1 produced in Reference Example 1 described later is used.

As the short term sustained-release microcapsule (C), specifically, a microcapsule (MC) #3 produced in Reference Example 3 described later is used.

In order to formulate the microcapsule into an injectable, a sustained-released injectable which can be actually used is obtained by formulating the microcapsule together with a dispersant (e.g. Tween 80, HCO-60, carboxymethylcellulose, sodium alginate, etc.), a preservative (e.g. methylparaben, propylparaben, etc.), and an isotonizing agent (e.g. sodium chloride, mannitol, sorbitol, glucose, etc.) into an aqueous suspension, or suspending the microcapsule together with a vegetable oil such as sesame oil and corn oil to obtain an oily suspension.

As the sustained-release preparation of the present invention, a combination of a preparation obtained by formulating a microcapsule which gradually releases a GnRH agonist or a salt thereof for a long term, into a sustained-release preparation, in particular, a preparation as the sustained-release injectable as described above, and a preparation obtained by formulating a microcapsule which gradually releases a GnRH agonist or a salt thereof for a short term, into a sustained-release preparation, in particular, a preparation as the sustained-release injectable as described above may be used. In addition, a preparation obtained by formulating microcapsules obtained by mixing a microcapsule which gradually releases a GnRH agonist or a salt thereof for a long term and a microcapsule which gradually releases a GnRH agonist or a salt thereof, into a sustained-release preparation, in particular, a preparation as the sustained-release injectable as described above may be used.

The said preparation containing a GnRH agonist (preferably leuprorelin or a salt thereof, more preferably leuprorelin acetate) (preferably, a preparation containing a sustained-release microcapsule containing leuprorelin or a salt thereof (preferably leuprorelin acetate)) can be directly, easily administered subcutaneously, intramuscularly or intravascularly (preferably subcutaneously and intramuscularly) as an injectable, etc.

Similarly, The sustained-release preparation of the present invention can be directly, easily administered subcutaneously, intramuscularly or intravascularly (preferably, subcutaneously and intramuscularly) as an injectable, etc. In the present invention, when a preparation obtained by formulating a mixture of a short time sustained-release microcapsule and a long term sustained-release microcapsule into a preparation, or a preparation obtained by mixing a short term sustained-release preparation and a long term sustained-release preparation into a preparation is administered, it can be easily administered, as such, subcutaneously, intramuscularly, or intravascularly (preferably subcutaneously and intramuscularly) as an injectable, etc. In addition, when a short term sustained-release preparation and a long term sustained-release preparation are administered separately, they can be directly, easily administered subcutaneously, intramuscularly or intravascularly (preferably, subcutaneously and intramuscularly). Usually the same administration route is selected, but the short term sustained-release preparation and the long term sustained-release preparation may also be administered by separate route such as subcutaneous and intramuscular routes, occasionally.

A dose of the preparation is variously different depending on content and dosage form of a GnRH agonist (preferably, leuprorelin or a salt thereof, more preferably leuprorelin acetate), duration of a GnRH agonist (preferably, leuprorelin or a salt thereof, more preferably leuprorelin acetate), and an animal to be administered [e.g. warm-blooded mammal (e.g. human, mouse, rat, rabbit, sheep, pig, cow, horse, etc.)], and may be an effective amount as a medicine of the GnRH agonist (preferably, leuprorelin or a salt thereof, more preferably leuprorelin acetate). For example, daily dosage for the warm-blooded mammal can be appropriately selected from a range of about 0.01 mg to 100 mg/kg body weight, preferably about 0.02 mg to 50 mg/kg body weight, further preferably 0.05 mg to 20 mg/kg body weight.

When the preparation is administered as an injectable, usually about 0.01 to 50 mg, preferably about 0.1 to 20 mg, more preferably about 0.1 to 15 mg of a GnRH agonist (preferably, leuprorelin or a salt thereof, more preferably leuprorelin acetate) may be subcutaneously or intramuscularly administered to an adult prostate cancer patient (weight 60 kg) per day. In addition, when administered as an injectable containing a sustained-release microcapsule containing the GnRH agonist (preferably, leuprorelin or a salt thereof, more preferably leuprorelin acetate), a dose is different depending on a drug sustained-release term of the sustained-release microcapsule. For example, when administered about once a month, usually about 0.01 to 25 mg, preferably about 0.1 to 15 mg, more preferably about 0.1 to 10 mg of a GnRH agonist (preferably, leuprorelin or a salt thereof, more preferably leuprorelin acetate) may be subcutaneously or intramuscularly administered to an adult prostate cancer patient (weight 60 kg) per one time. For example, when administered once in about 3 months, usually about 0.1 to 75 mg, preferably about 0.1 to 45 mg, more preferably about 1 to 30 mg of a GnRH agonist (preferably, leuprorelin or a salt thereof, more preferably leuprorelin acetate) may be subcutaneously or intramuscularly administered to an adult prostate cancer patient (weight 60 kg) per one time. For example, administered once for about 6 months, usually about 0.2 to 150 mg, preferably about 0.2 to 90 mg, more preferably about 2 to 60 mg of a GnRH agonist (preferably, leuprorelin or a salt thereof, more preferably leuprorelin acetate) may be subcutaneously or intramuscularly administered to an adult prostate cancer patient (weight 60 kg) per one time.

Also in the case of other animals, an amount obtained by converting into an amount per weight 60 kg may be administered, and can be administered by appropriately increasing or decreasing the aforementioned dose depending on sustained-release term.

The preparation comprising a combination of the short term sustained-release microcapsule and the long term sustained-release microcapsule of the present invention can be administered by converting the aforementioned dose of a GnRH agonist from a sustained-release term of the long term sustained-release microcapsule, and appropriately distributing into the short term sustained-release microcapsule and the long term sustained-release microcapsule.

When amino acids, peptides, and protecting groups in polypeptides described herein are expressed by abbreviation, this is based on abbreviation by IUPAC-IUB Commission on Biochemical Nomenclature or the conventional abbreviation in the art. In addition, when the amino acid can have an optical isomer, an L-isomer is denoted unless otherwise indicated.

Examples of abbreviation are shown below:

Abu: Aminobutyric acid

Aibu: 2-Aminobutryric acid

Ala: Alanine

Arg: Arginine

Gly: Glycine

His: Histidine

Ile: Isoleucine

Leu: Leucine

Met: Methionine

Nle: Norleucine

Nval: Norvaline

Phe: Phenylalanine

Phg: Phenylglycine

Pro: Proline (Pyr)Glu: Pyroglutamic acid

Ser: Serine

Thr: Threonine

Trp: Tryptophan

Tyr: Tyrosine

Val: Valine

D2Nal: D-3-(2-napthyl)alanine residue

DSer(tBu): O-tert-butyl-D-serine

DHis (ImBzl): $N^{im}$-benzyl-D-histidine

PAM: Phenylacetamidomethyl

Boc: t-butyloxycarbonyl

Fmoc: 9-Fluorenylmethyloxycarbonyl

Cl-Z: 2-Chloro-benzyloxycarbonyl

Br-Z: 2-Bromo-benzyloxycarbonyl

Bzl: Benzyl $Cl_2$-Bzl: 2,6-Dichlorobenzyl

Tos: p-toluenesulfonyl

HONb: N-hydroxy-5-norbornene-2,3-dicarboxyimide

HOBt: 1-Hydroxybenzotriazole

HOOBt: 3-Hydroxy-3,4-dihydro-4-oxo-1,2,3-benzotriazine

MeBzl: 4-Methylbenzyl

Bom: Benzyloxymethyl

Bum: t-butoxymethyl

Trt: Trityl

DNP: Dinitrophenyl

DCC: N,N'-dicyclohexylcarbodiimide

EXAMPLES

The following Examples including Experimental Examples will illustrate the present invention more specifically.

Reference Example 1

Production of Microcapsule (B)

119.1 g of 5-oxo-Pro-His-Trp-Ser-Tyr-Dleu-Leu-Arg-Pro-NH—$C_2H_5$ (SEQ ID NO: 2) (hereinafter, abbreviated as peptide A) acetate was weighed in an eggplant-type flask, and 120 g of water for injection was added to dissolve it completely. To this was added 975 g of a lactic acid-glycolic acid copolymer (lactic acid•glycolic acid compositional ratio=75:25, Mw=about 10,400, Mn=about 4,100, Mw/Mn=2.5 (value measured by GPC method in Reference Example 5 (value measured using standard substance C))) dissolved in 1600 g of dichloromethane, and this was stirred and emulsified with an autominimixer at about 5800 rpm for 10 minutes to obtain a W/O emulsion. This W/O emulsion was cooled to about 19° C., poured into 200 L of a 0.1% (w/w) aqueous polyvinyl alcohol (EG-40, manufactured by The Nippon Synthetic Chemical Industry Co., Ltd.) solution which had been regulated at about 19° C. in advance, and stirred and emulsified at about 7000 rpm using HOMOMIC LINE FLOW (manufactured by Tokushu Kika Kogyo Co., Ltd.) to obtain a W/O/W emulsion. This W/O/W emulsion was stirred at room temperature at about 2500 rpm for 3 hours and dichloromethane was volatilized or diffused into an outer aqueous phase to solidify an oil phase. After passed through a sieve having an opening of 75 μm, a microcapsule was continuously settled with a centrifuge at about 2000 rpm and collected. The collected microcapsule was dispersed in a small amount of distilled water, and passed through a sieve having an opening of 90 μm, and 174.5 g of mannitol was added to dissolve it. This was lyophilized to obtain a microcapsule powder (hereinafter, MC#1). A content of the peptide A was 8.5%.

Reference Example 2

Production of Microcapsule (A)

123.3 g of peptide A acetate was weighed in an eggplant-type flask, and 129.4 g of a 2 wt % aqueous acetic acid solution was added to dissolve it completely. To this was added 1080 g of a DL-lactic acid polymer (Mw=about 21,400 (value measured using standard substance B)) dissolved in 1890 g of dichloromethane, roughly dispersed for about 2 minutes, and stirred and emulsified with an autominimixer at about 5800 rpm for 4 minutes to obtain a W/O emulsion. This W/O emulsion was cooled to about 18° C., poured into 200 L of a 0.1 wt % polyvinyl alcohol (EG-40, manufactured by The Nippon Synthetic Chemical Industry Co., Ltd.) solution containing 1 wt % aqueous mannitol which had been regulated at about 18° C. in advance, and stirred and emulsified at about 7000 rpm using HOMOMIC LINE FLOW (manufactured by Tokushu Kika Kogyo Co., Ltd.) to obtain a W/O/W emulsion. This W/O/W emulsion was stirred at room temperature at about 2500 rpm for 3 hours, dichloromethane was volatilized diffused into an outer aqueous phase to solidify an oil phase. After passed through a sieve having an opening of 75 μm, a microcapsule was continuously settled with a centrifuge at about 2000 rpm, and this was collected. The collected microcapsule was dispersed in a small amount of distilled water, and passed through a sieve having an opening of 90 μm, and 169.7 g of mannitol was added to dissolve it. This was lyophilized to obtain a microcapsule powder (hereinafter, MC#2). A content of the peptide was 7.5%.

Reference Example 3

Production of Microcapsule (C)

86.7 g of peptide A acetate was weighed in an eggplant-type Kolben, and 100 g of water for injection was added to dissolve it completely. To this was added 765 g of DL-lactic acid polymer (Mw=about 14,200 (value measured using standard substance A)) dissolved in 1280 g of dichloromethane, and stirred and emulsified with an autominimixer at 5800 rpm for 13.5 minutes to obtain a W/O emulsion. This W/O emulsion was cooled to about 15° C., poured into 200 L of a 0.1% (w/w) aqueous polyvinyl alcohol (EG-40, manufactured by The Nippon Synthetic Chemical Industry Co., Ltd.) which had been regulated at about 15° C. in advance, and stirred and emulsified at about 7000 rpm using HOMOMIC LINE FLOW (manufactured by Tokushu Kika Kogyo Co., Ltd.) to obtain a W/O/W emulsion. This W/O/W emulsion was stirred at room temperature at about 2500 rpm for 3 hours, and dichloromethane was volatilized or diffused into an outer aqueous phase to solidify an oil phase. After passed through a sieve having an opening of 75 μm, a microcapsule was continuously settled with a centrifuge at about 2000 rpm and collected. The collected microcapsule was dispersed in a small amount of distilled water, passed through a sieve having an opening of 90 μm, and 130 g of mannitol was added to dissolve it. This was lyophilized under the secondary drying condition at 50° C. for 48 hours to obtain a microcapsule powder (hereinafter, MC#3). A content of the peptide was 7.8%.

Reference Example 4

Production of Microcapsule (C)

14.5 g of peptide A acetate was weighed in eggplant-type Kolben, and 15.9 g of water for injection was added to dissolve it completely. To this was added 123 g of DL-lactic acid polymer (Mw=about 14,100) dissolved in 204 g of dichloromethane, roughly emulsified for 1 minute, and stirred and emulsified with an autominimixer at about 10000 rpm for 3 minutes to obtain a W/O emulsion. This W/O emulsion was cooled to about 16° C., poured into 25 L of 0.1% (w/w) aqueous polyvinyl alcohol (EG-40, manufactured by The Nippon Synthetic Chemical Industry Co., Ltd.) solution which had been regulated at about 16° C. in advance, and stirred and emulsified at about 7000 rpm using HOMOMIC LINE FLOW (manufactured by Tokushu Kika Kogyo Co., Ltd.) to obtain a W/O/W emulsion. This W/O/W emulsion was stirred at room temperature at about 2000 rpm for 3 hours and dichloromethane was volatilized or diffused in an outer aqueous phase to solidify an oil phase. After passed through a sieve having an opening of 75 μm, a microcapsule was continuously settled with a centrifuge at 2000 rpm and collected. The collected microcapsule was dispersed in a small amount of distilled water, passed through a sieve having an opening of 90 μm, and 17.5 g of mannitol was added to dissolve it. This was lyophilized under the secondary drying temperature condition at 50° C. for a secondary drying time of 0 hour, 20 hours, 22 hours, 24 hours, 26 hours and 48 hours, to collect each microcapsule powder separately.

Reference Example 5

Measurement of Weight Average Molecular Weight (Mw) of Polymer (GPC Method)

About 0.05 g of this product is weighed, tetrahydrofuran (THF) is added to dissolve it to 5 mL, and a sample solution is obtained.

Separately, each about 0.1 g of polystyrene standard products (F-10, F-2, A-5000 and A-1000) having the known molecular weights is weighed, THF is added to dissolve it to 40 mL, and a standard solution A is obtained. In addition, each about 0.1 g of polystyrene standard products (F-4, F-1, A-2500 and A-500) having the known molecular weights is weighed, THF is added to dissolve it to 40 mL, and a standard solution B is obtained.

100 μL each of the sample solution and the standard solutions A and B are tested by a gel permeation chromatography method under the following conditions. From a molecular weight of each polystyrene standard product and its retention time, a molecular weight calibration curve is produced. Then, a peak height (Hi) of an eluted component obtained from the sample solution is measured, and its molecular weight (Mi) is obtained from its retention time and the calibration curve. A weight average molecular weight (Mw) of the present product is obtained from the following equation.

$$Mw = \Sigma(Hi \times Mi)/\Sigma Hi \quad \text{[Calculation equation]}$$

[Test Condition]

Detector: differential refractometer (having performance equivalent to that of HLC-8120GPC system)

Column: TSK guardcolumn $H_{HR}$-L (40×6.0 mm i.d.)
  gel G40000$H_{HR}$ (300×7.8 mm i.d.)
  gel G3000$H_{HR}$ (300×7.8 mm i.d.)
  gel G2000$H_{HR}$ (300×7.8 mm i.d.), and
  gel G1000$H_{HR}$ (300×7.8 mm i.d.)
are connected in a series in an order of reduction in a pore diameter of a filler (or those having the similar performance can be used).

Column temperature: a constant temperature around 50° C.

Mobile phase: THF

Flow rate: 1.0 mL/min

[System Suitability]

(1) Performance of System:
  When the system is operated on 100 μL of the standard solution A under the aforementioned conditions, a separation degree between a peak of F-10 and a peak of F-2 is 2.0 or more, and a theoretical step number and a symmetry coefficient of both peaks are 800 step or more and 1.5 or less, respectively.

(2) Reproducibility of Test:
  When the test is repeated twice on 100 μL of the standard solution A under the aforementioned conditions, a relative standard deviation between retention times of each peak is 3.3% or less.

[Operation Method]
  Standard solution: The solution is stable at room temperature (about 25° C.) within at least 24 hours after preparation. In addition, the solution is stable for at least 7 months in a refrigerator (about −18° C.) after preparation.

Sample solution: The solution is stable at room temperature (about 25° C.) within at least 24 hours after preparation. Range of area measurement: 48 minutes (injection interval is 50 minutes)

Molecular weight calibration curve: it is produced by a polygonal line.

In addition to a weight average molecular weight (Mw), a number average molecular weight [Mn=ΣHi/Σ(Hi/Mi)] is also measured.

[Injection Order]
  (1) A test is repeated twice on a standard solution A, and it is confirmed that the first test adapts to the rule of performance of the system. A retention time of each peak is obtained, and it is confirmed that this adapts to the rule of reproducibility of the test (a relative standard deviation between retention times of respective peaks is 3.3% or less).

(2) A standard solution B is injected, and a retention time of each peak is obtained.

(3) A mobile phase is injected, a carryover of all peaks of the standard solution B injected in (2) is checked, and it is confirmed that a peak area value satisfies specification (10% or less).

(4) Measurement of sample solution (maximum 12)

(5) A mobile phase is injected, a carryover of the sample solution finally injected in (4) is checked, and it is confirmed that a peak area value adapts to the rule (10% or less).

(6) The standard solutions A and B are injected, and a retention time of each molecular weight is obtained.

(7) A molecular weight calibration curve is produced from retention times of the standard solution A finally injected in (1), the standard solution B injected in (2), and standard solutions A and B injected in (6), and a weight average molecular weight (Mw) of the sample is calculated, provided that it is confirmed that a relative deviation of retention times [RD: % of a difference (absolute value) from an average value of any retention time relative to an average value] of the standard solution A finally injected in (1) and the standard solution A injected in (6) is 3.3% or less. When it is not adapted, all data between system checks are invalidated, and the test is performed again from (1) (provided that it is not necessary to investigate performance of system).

[Reagent•Test Solution]

Polystyrene standard products: TSK standard polystyrene/ manufactured by Tosoh Corporation As Mw of polystyrene standard products, values assessed by a GPC method are used.

| Type | Mw |
|---|---|
| F-10 | 98900 |
| F-4 | 37200 |
| F-2 | 17100 |
| F-1 | 9490 |
| A-5000 | 5870 |
| A-2500 | 2500 |
| A-1000 | 1051 |
| A-500 | 495 |

Tetrahydrofuran: for liquid chromatography, manufactured by Wako Pure Chemical Industries, Ltd.

Example 1

To 0.141 g of MC#1 (peptide A acetate content 8.5%) produced in Reference Example 1, 1.920 g of MC#2 (peptide A acetate content 7.5%) produced in Reference Example 2 was added and the materials were mixed to prepare two-kind mixed type microcapsule powder (hereinafter, combo A). Thereupon, a combination ratio was 1 to 12 (as weight ratio of peptide A acetate).

Example 2

To 0.184 g of MC#3 (peptide A acetate content 7.8%) produced in Reference Example 3, 1.20 g of MC#2 (peptide A acetate content 7.5%) produced in Reference Example 2 was added and mixed to prepare two-kind mixed type microcapsule (hereinafter, combo B). Thereupon, a combination ratio was 1 to 9 (as weight ratio of peptide A acetate).

Example 3

To 0.154 g of MC#3 (peptide A acetate content 7.8%) produced in Reference Example 3, 1.920 g of MC#2 (peptide A acetate content 7.5%) produced in Reference Example 2 was added and mixed to prepare two-kind mixed type microcapsule powder (hereinafter, combo C). Thereupon, a combination ratio was 1 to 12 (as weight ratio of peptide A acetate).

Example 4

To 0.141 g of MC#1 (peptide A acetate content 8.5%) produced in Reference Example 1, 2.560 g of MC#2 (peptide A acetate content 7.5%) produced in Reference Example 2 was added and mixed to prepare two-kind mixed type microcapsule powder (hereinafter, combo D). Thereupon, a combination ratio was 1 to 16 (as weight ratio of peptide A).

Experimental Example 1

120 mg of combo B, the two-kind mixed type microcapsule powder produced in Example 2 (9 mg as peptide A acetate) was suspended in about 0.3 mL of a dispersing medium, the suspension was injected into a rat subcutaneously, and a concentration of peptide A in serum was measured. 120 mg of MC#2 (9 mg as peptide A acetate) was suspended in about 0.3 mL of a dispersing medium, and the similar test was performed in another rat. The change in blood concentration of combo B was compared with that of one kind alone. Change in blood concentration until 5 week after administration is shown in FIG. 1. When blood concentrations within 1 week after administration were compared, combo B hovered at a higher value than that of MC#2, both had different sustained-release rates, and the effect on sustained-release of the 2 kind mixed type microcapsule was confirmed.

Experimental Example 2

Figure 2:
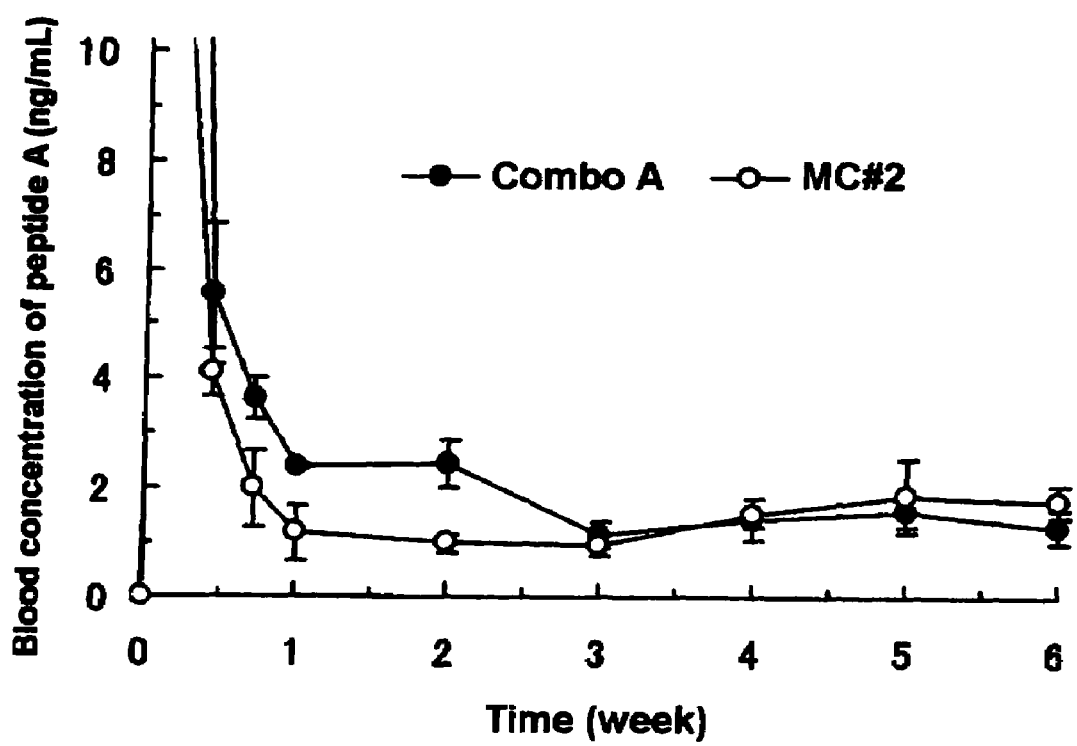
FIG. 2 is a graph showing results of Experimental Example 2. ● denotes a blood concentration of peptide A when combo A is administered, and ○ denotes a blood concentration of peptide A when MC#2 is administered.

129 mg of combo A, the two-kind mixed type microcapsule powder produced in Example 1 (9.75 mg as peptide A acetate) was suspended in about 0.3 mL of a dispersing medium, the suspension was injected into a rat subcutaneously, and a concentration of peptide A in serum was measured. 120 mg of MC#2 (9 mg as peptide A acetate) was suspended in about 0.3 mL of a dispersing medium, the similar test was performed on another rat. The change in blood concentration of combo A was compared with that of one kind alone. Change in blood concentration until 6 week after administration is shown in FIG. 2. When blood concentrations within 3 weeks after administration were compared, combo A hovered at a higher value than that of MC#2, both had different sustained-release rates, and the effect on sustained-release of the two-kind mixed type microcapsule was confirmed.

Experimental Example 3

Figure 3:
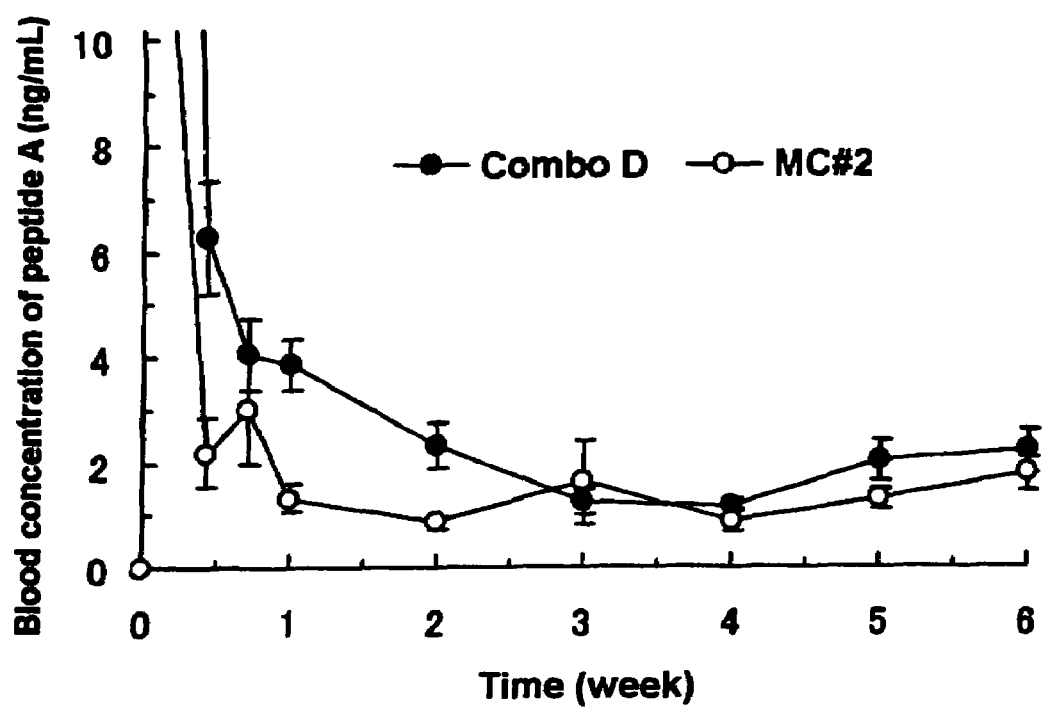
FIG. 3 is a graph showing results of Experimental Example 3. ● denotes a blood concentration of peptide A when combo D is administered, and ○ denotes a blood concentration of peptide A when MC#2 is administered.

169 mg of combo D, the two-kind mixed type microcapsule powder produced in Example 4 (12.75 mg as peptide A acetate) was suspended in about 0.3 mL of a dispersing medium, the suspension was injected into a rat subcutaneously, and a concentration of peptide A in serum was measured. 120 mg of MC#2 (9 mg as peptide A acetate) was suspended in about 0.3 mL of a dispersing medium, the similar test was performed on another rat. The change in blood concentration of combo D was compared with that of one kind alone. Change in blood concentration until 6 week after administration is shown in FIG. 3. When blood concentrations within 3 weeks after administration were compared, combo D hovered at a higher value than that of MC#2, both had different sustained-release rates, and the effect on sustained-release of the two-kind mixed type microcapsule was confirmed.

INDUSTRIAL APPLICABILITY

By combining microcapsules which gradually release a GnRH agonist or a salt thereof and have different sustained-release terms, a preparation excellent in sustained-release which has increased amount of drug release at an early stage of administration, and releases a constant amount of the drug over a long term can be obtained.

All publications, patents and patent applications identified above are herein incorporated by reference.

Although the invention has been described above by reference to certain embodiments of the invention, the invention is not limited to the embodiments described above. Modifications and variations of the embodiments described above falling within the scope of the invention will occur to those skilled in the art, in light of the teachings. The scope of the invention is defined solely with reference to the following claims.

The invention claimed is:

1. A sustained release preparation comprising a combination of first microcapsules which gradually release a GnRH agonist or a salt thereof for 5 to 8 months, and second microcapsules which gradually release a GnRH agonist or a salt thereof for 1 week to 5 months so that blood concentration of the GnRH agonist within one week after administration is about 2 ng/mL or higher, wherein:
   (a) the first microcapsules comprise:
      (i) a GnRH agonist or a salt thereof, and
      (ii) a lactic acid polymer having a weight-average molecular weight of about 18,000 to about 30,000; and
   (b) the second microcapsules comprise:
      (i) a GnRH agonist or a salt thereof, and
      (ii) a lactic acid-glycolic acid polymer (75/25 (mol %)) having a weight-average molecular weight of 8,000 to about 12,000, or a lactic acid polymer having a weight-average molecular weight of about 13,000 to about 18,000, wherein the ratio of first microcapsule to second microcapsule is from 5:1 to 20:1 expressed as weight ratios of the GnRH agonist or a salt thereof.

2. The preparation according to claim 1, wherein the GnRH agonist or a salt thereof is a peptide represented by the formula of SEQ ID NO: 1:

5-oxo-Pro-His-Trp-Ser-Tyr-Y-Leu-Arg-PrO-Z wherein Y represents a residue selected from DLeu, DAla, DTrp, DSer (tBu), D2Nal and DHis (ImBzl), and Z represents NH—$C_2H_5$ or Gly-$NH_2$
or a salt thereof.

3. The preparation according to claim 1, wherein the GnRH agonist or a salt thereof is an acetate of a peptide of the formula of SEQ ID NO: 2:

5-oxo-Pro-His-Trp-Ser-Tyr-Dleu-Leu-Arg-Pro-NH—$C_2H_5$.

4. The sustained-release preparation according to claim 1, which gradually releases a substantially constant amount of a GnRH agonist or a salt thereof for 5 months or longer.

5. A composition comprising:
   (a) a pharmaceutically effective amount of the sustained-release preparation according to claim 1, and
   (b) a pharmaceutically acceptable excipient.

6. A process for producing the sustained-release preparation according to claim 1, which comprises mixing the first and second microcapsules.

7. A method for treating prostate cancer, prostatomegaly, endometriosis, hysteromyoma, metrofibroma, precocious puberty, dymenorrhea or breast cancer, or inhibiting conception, comprising administering an effective amount of the sustained-release preparation according to claim 1 to a mammal in need thereof.

8. The preparation according to claim 1, wherein:
   (a) the first microcapsules comprise:
      (i) a GnRH agonist or a salt thereof, and
      (ii) a lactic acid polymer having a weight-average molecular weight of about 21400; and
   (b) the second microcapsules:
      (1) comprise (i) a GnRH agonist or a salt thereof, and (ii) a lactic acid-glycolic acid polymer (75/25 (mol %)) having a weight-average molecular weight of about 10400, or
      (2) comprise (i) a GnRH agonist or a salt thereof, and (ii) a lactic acid polymer having a weight-average molecular weight of about 14200.

* * * * *